United States Patent
Worth et al.

(10) Patent No.: US 11,458,201 B2
(45) Date of Patent: Oct. 4, 2022

(54) MUCOSAL ACTIVE AGENT DELIVERY

(71) Applicant: Suda Ltd., Osborne Park (AU)

(72) Inventors: Carol Worth, Shenton Park (AU); Kalpana Baride, Canning Vale (AU)

(73) Assignee: Suda Ltd., Osborne Park (AU)

(*) Notice: Subject to any disclaimer, the term of this patent is extended or adjusted under 35 U.S.C. 154(b) by 178 days.

(21) Appl. No.: 16/345,098

(22) PCT Filed: Oct. 30, 2017

(86) PCT No.: PCT/AU2017/051193
§ 371 (c)(1),
(2) Date: Apr. 25, 2019

(87) PCT Pub. No.: WO2018/076074
PCT Pub. Date: May 3, 2018

(65) Prior Publication Data
US 2019/0282697 A1    Sep. 19, 2019

(30) Foreign Application Priority Data
Oct. 31, 2016  (AU) .............................. 2016904449

(51) Int. Cl.
*A61K 47/22* (2006.01)
*A61K 31/138* (2006.01)
*A61K 31/192* (2006.01)
*A61K 31/196* (2006.01)
*A61K 31/4045* (2006.01)
*A61K 31/4178* (2006.01)
*A61K 31/437* (2006.01)
*A61K 31/4402* (2006.01)
*A61K 31/519* (2006.01)
*A61K 47/12* (2006.01)
*A61P 1/08* (2006.01)
*A61P 15/10* (2006.01)
*A61K 9/00* (2006.01)
*A61K 31/135* (2006.01)
*A61P 9/12* (2006.01)

(52) U.S. Cl.
CPC .............. *A61K 47/22* (2013.01); *A61K 9/006* (2013.01); *A61K 31/135* (2013.01); *A61K 31/138* (2013.01); *A61K 31/192* (2013.01); *A61K 31/196* (2013.01); *A61K 31/4045* (2013.01); *A61K 31/4178* (2013.01); *A61K 31/437* (2013.01); *A61K 31/4402* (2013.01); *A61K 31/519* (2013.01); *A61K 47/12* (2013.01); *A61P 1/08* (2018.01); *A61P 9/12* (2018.01); *A61P 15/10* (2018.01)

(58) Field of Classification Search
None
See application file for complete search history.

(56) References Cited

U.S. PATENT DOCUMENTS

| | | |
|---|---|---|
| 2002/0019898 A1 | 2/2002 | Hayashi et al. |
| 2003/0158206 A1 | 8/2003 | Billotte et al. |
| 2007/0275929 A1 | 11/2007 | Fuls et al. |
| 2008/0145390 A1 | 6/2008 | Taylor et al. |
| 2010/0204323 A1 | 8/2010 | Theiler et al. |
| 2015/0250791 A1 | 9/2015 | Sa et al. |
| 2016/0166543 A1 | 6/2016 | Joshi et al. |

FOREIGN PATENT DOCUMENTS

| | | |
|---|---|---|
| WO | WO-2005/032520 A1 | 4/2005 |
| WO | WO-2011/156405 A2 | 12/2011 |
| WO | WO-2013/085904 A1 | 6/2013 |

OTHER PUBLICATIONS

Prousky et al. (The treatment of migraines and tension-type headaches with intravenous and oral niacin (nicotinic acid): systematic review of the literature. Nutr J. Jan. 26, 2005;4:3).*
Cosmetic Ingredient Review Expert Panel. Final report of the safety assessment of niacinamide and niacin. Int J Toxicol. 2005;24 Suppl 5:1-31.*
Beig et al., Oral delivery of lipophilic drugs: the tradeoff between solubility increase and permeability decrease when using cyclodextrin-based formulations, *PLoS One.* 8:068237 (2013).
Gennaro et al., Remington: The Science and Practice of Pharmacy, Lippincott Williams & Wilkins (20th ed. 2000).
Herbig et al., Correlation of hydrotropic solubilization by urea with log D of drug molecules and utilization of this effect for topical formulations, *European Journal of Pharmaceutics and Biopharmaceutics*, 85:158-160 (2013).
Higuchi et al., Binding specificity between small organic solutes in aqueous solution: classification of some solutes into two groups according to binding tendencies, *J. Pharm. Sci.* 59:1601-8 (1970).
International Application No. PCT/AU2017/051193, International Preliminary Reporton Patentability, dated Apr. 30, 2019.
International Application No. PCT/AU2017/051193, International Search Report and Written Opinion, dated Nov. 27, 2017.
Lachman et al., Theory of Practice of Industrial Pharmacy, Lippincott Williams & Wilkins (3rd ed. 1986).
Narang et al., Targeted Delivery of Small and Macromolecular Active Agents, pp. 524 (2010).
Nicolazzo et al., Buccal penetration enhancers—How do they really work? Journal of Controlled Release. 105:1-15(2005).
Swarbrick et al., Encyclopedia of Pharmaceutical Technology, Marcel Dekker (2nd ed. 2002).

* cited by examiner

*Primary Examiner* — Layla Soroush
(74) *Attorney, Agent, or Firm* — Marshall, Gerstein & Borun LLP

(57) ABSTRACT

A method to increase the penetration of active agents through mucosal membranes, the method comprising the step of: a) administering to a subject in need a composition comprising: i) one or more hydrotropes in a total amount of less than 15% by weight of the composition; and ii) an active agent with a partition co-efficient (log P) or distribution coefficient (log D) of between 0 and 5.

8 Claims, 17 Drawing Sheets

Caffeine　　　　　　　　　Nicotinamide (and derivatives)

Sodium benzoate　　　　　　　　Ascorbic acid

Sodium salicylate

Sildenafil

Oestradiol

Carvedilol

Sumatriptan

Zolpidem

Ibuprofen

Diclofenac

Ondansetron

Midazolam

MUCOSAL ACTIVE AGENT DELIVERY

This application is a U.S. National Phase of International Application No. PCT/AU2017/051193 filed Oct. 30, 2017, which claims priority from Application No. 2016904449 filed on Oct. 31, 2016 in Australia. The entire contents of these applications are incorporated herein by reference in their entirety.

TECHNICAL FIELD

A method for modifying the penetration of active agents through mucosal membranes using hydrotropes.

BACKGROUND ART

The mucosal membranes of the body are a useful site for the delivery of active agents in the systemic circulation, as direct drainage of blood from the epithelium into the circulatory system avoids first pass metabolism in the liver seen after intestinal absorption.

Nevertheless, the structure and chemical properties of mucosal surfaces can inhibit the passive transport of many active agents.

For example, the oral mucosa acts as a barrier to active agents and other foreign agents. The oral cavity has a stratified mucosa with both keratinised (palate and gingiva) and non-keratinised regions. The main permeability barrier in the oral mucosa is considered to be due to the membrane coating granules (MCG) which protrude into the intercellular spaces in the upper third of the epithelium. In investigation of porcine tissue, non-keratinised buccal and sublingual mucosa were found to contain high quantities of the more polar phospholipids, cholesterol esters and glycosylceramides, and minimal amounts of the less polar ceramides normally found in epidermis and keratinised oral mucosa. The extrusion of contents from the MCG means that the intercellular spaces are filled with an amorphous conglomeration of polar lipids with occasional short stacks of lipid lamellae, collectively termed lipid fractions. Permeability has been shown to be limited by the mucosal layers containing MCG. As described above, the buccal mucosal epithelia consist of epithelial cells surrounded by a hydrophilic intercellular matrix filled with polar lipids in an amorphous state with occasional short stacks of lipid lamellae. Thus the lipophilic cell membranes of the epithelial cells are surrounded by relatively polar intercellular lipids on the cell exterior and hydrophilic aqueous cytoplasm in the cell interior.

It has commonly been thought that there are two permeation pathways for passive transport of active agents across the mucosal membranes: (i) between the cells via the intercellular (paracellular) route; or (ii) via the transcellular route (i.e. penetration and movement through the intracellular spaces of the cells). These two routes may be used simultaneously but, depending on the physiochemical nature of the active agent, one normally predominates. It was believed that hydrophilic active agents would have difficulty permeating through the lipid-rich cell membrane and would therefore travel the intercellular route; and the hydrophilic intercellular spaces would present a barrier to lipophilic active agents and they would therefore travel the transcellular route.

However, recent evidence suggests that most compounds actually transverse the mucosal membranes via the intercellular (paracellular) route. Thus the movement of both hydrophilic and lipophilic active agents is through this intercellular route. The hydrophilic active agents move via non-lipidic regions in the intercellular spaces, but may find it difficult to penetrate the tight spaces between the cell membranes. Lipophilic active agents also move through the intercellular spaces, by interaction with the lipid cell plasma membranes lining the intercellular space and the lipid fraction extruded by the MCG into the intercellular space, with transition times dependent on degree of binding of active to those lipids.

Mucosal drug delivery permeation problems may be summarised as:
insufficient initial partitioning of drug into the mucosal tissue; and/or
interaction of drugs with intercellular lipids, cell membrane lipids and/or epithelial protein domains.

Enhancement of active agent transport must therefore take into account the physiochemical properties of the active agent and interactions that may be occurring within the intercellular space. The present invention seeks to address these parameters and provide an alternative method for increasing the penetration of active agents across mucosal membranes.

The above discussion of the background art is intended to facilitate an understanding of the present invention only. The discussion is not an acknowledgement or admission that any of the material referred to is or was part of the common general knowledge as at the priority date of the application.

SUMMARY OF INVENTION

The present invention provides a pharmaceutical composition for transmucosal delivery comprising:
   a) one or more hydrotropes in a total amount of less than 15% by weight of the composition; and
   b) an active agent with a partition co-efficient (log P) or distribution coefficient (log D) of between 0 and 5.

The composition of the present invention may further comprise a co-solvent.

The present invention provides a method to increase the penetration of active agents through mucosal membranes, the method comprising the step of:
   i) administering to a subject in need a pharmaceutical composition for transmucosal delivery comprising:
      a) one or more hydrotropes in a total amount of less than 15% by weight of the composition; and
      b) an active agent with a partition co-efficient (log P) or distribution coefficient (log D) of between 0 and 5.

The present invention provides a kit containing:
   a) one or more hydrotropes in a total amount of less than 15% by weight of the composition;
   b) an active agent with a partition co-efficient (log P) or distribution coefficient (log D) of between 0 and 5; and
instructions for use as a pharmaceutical composition for transmucosal delivery.

The present invention provides a therapeutic pharmaceutical composition for transmucosal delivery comprising:
   a) one or more hydrotropes in a total amount of less than 15% by weight of the composition;
   b) an active agent with a partition co-efficient (log P) or distribution coefficient (log D) of between 0 and 5; and
   c) pharmaceutically acceptable excipients.

The present invention provides a method to manufacture a pharmaceutical composition for the transmucosal delivery of an active agent with a partition co-efficient (log P) or distribution coefficient (log D) of between 0 and 5 to a subject in need thereof, in combination with one or more hydrotropes in a total amount of less than 15% by weight of the composition.

The present invention provides for the use of one or more hydrotropes in a total amount of less than 15% by weight of the composition for the manufacture of a pharmaceutical composition for the transmucosal delivery of an active agent with a log P or log D of between 0 and 5 to a subject in need thereof.

Preferably, the partition co-efficient (log P) or distribution coefficient (log D) of the active agents is between 0.5 and 3.0 and/or the hydrotropes are present in a total amount of less than 10% by weight of the composition.

BRIEF DESCRIPTION OF THE DRAWINGS

The description will be made with reference to the accompanying drawings in which.

Figure 1:
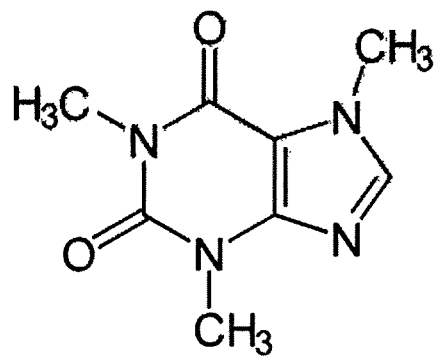
FIG. 1 provides drawings of representative examples of hydrotropes according to the present invention.
Figure 1:
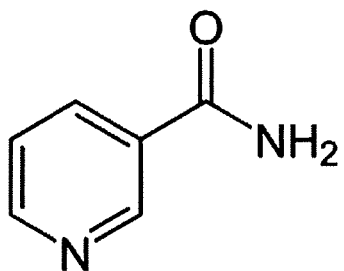
Figure 1:
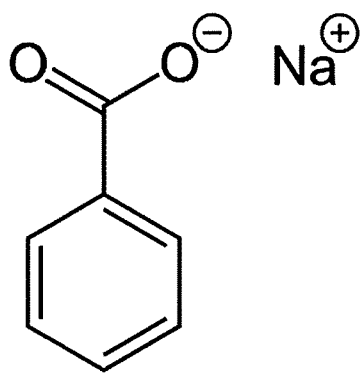
Figure 1:
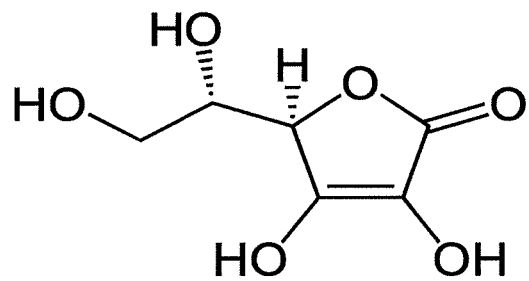
Figure 1:
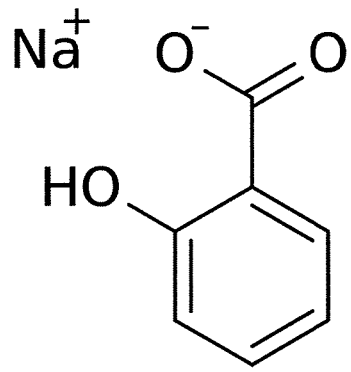
Figure 2A:
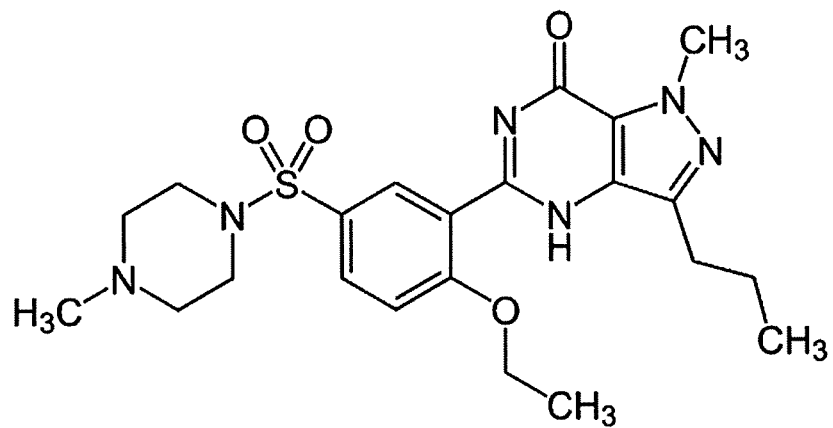
FIGS. 2A-C provides drawings of representative examples of active agents according to the present invention.
Figure 2A:
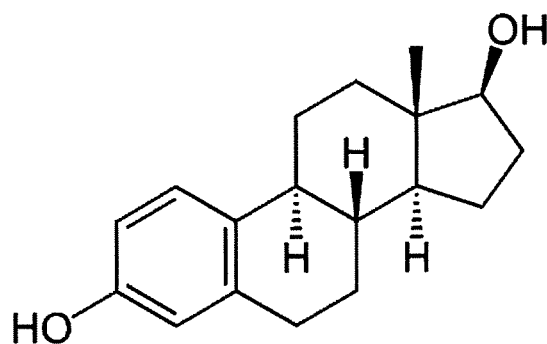
Figure 2A:
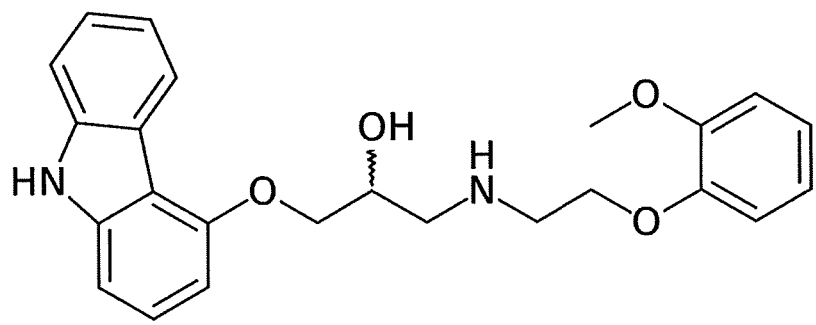
Figure 2B:
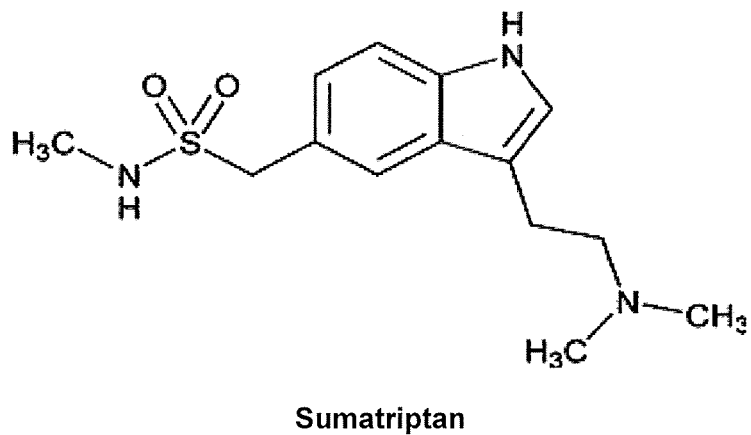
Figure 2B:
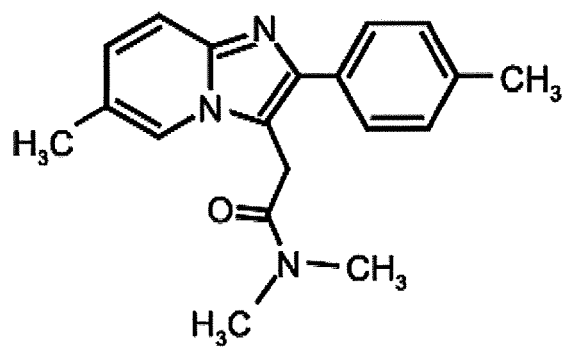
Figure 2B:
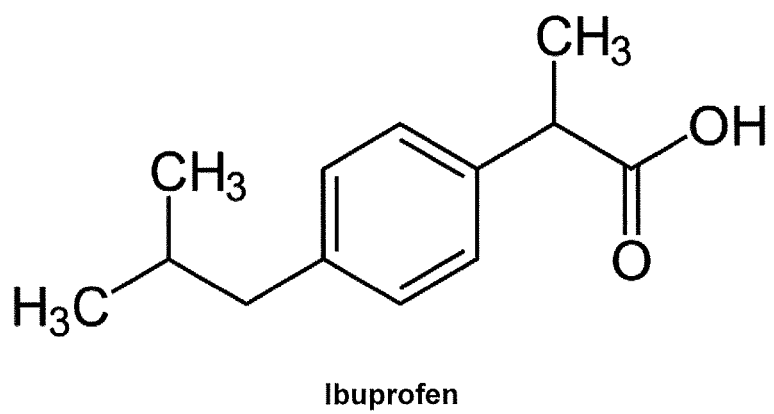
Figure 2C:
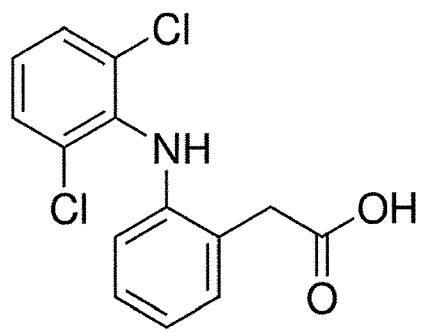
Figure 2C:
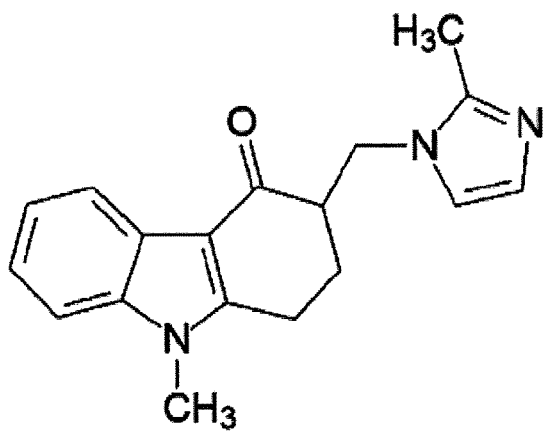
Figure 2C:
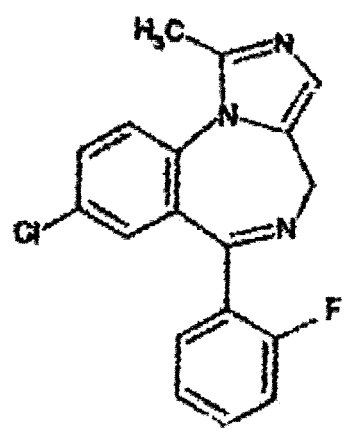

Base formulation—Group 1: circle; TF1—Group 2: square; TF2—Group 3 triangle. TF2 and TF3 have different flavour combinations

DESCRIPTION OF THE INVENTION

Detailed Description of the Invention

It has been postulated that active agents permeate the buccal mucosa via an intercellular route (Nicolazzo et al 2005). Highly lipophilic or non-polar compounds become associated with the cellular membrane lipids and other lipidic components as they permeate through the intercellular spaces. The nonpolar route for active agents involves lipid elements by partitioning of the active agent into the lipid bilayer of the plasma membrane or into the lipids of the intercellular matrix. The polar route involves passage of hydrophilic compounds through the ion channels in the intercellular spaces.

It is known that increasing the lipophilicity of active agents increases the transport of the active agents across the membranes of the body, including the intestinal epithelial cells and the blood brain barrier (BBB), until limits are reached. These limits are thought to be due to the increased binding of the active agents to the lipids in the membranes, so that active agents enter the membranes but do not exit. Highly lipophilic compounds also bind to other amphiphilic sites that may be found in plasma, including proteins.

Hydrotropes have long been used to increase solubility of poorly water-soluble drugs allowing those drugs to be dissolved in aqueous solutions at levels high enough to be useful formulations. This technology is directly applicable to injectable drugs, but directly leads to permeation problems with drugs which must pass through dermal, buccal or intestinal membranes.

Hydrotropes may be broadly defined as a class of compounds that are traditionally used to increase the aqueous solubility of sparingly soluble solutes. Typically, hydrotropes consist of a polar end and a non-polar end, but the non-polar end is generally too small to show spontaneous micellisation. Classifying hydrotropes based on molecular structure is difficult, as a wide variety of compounds exhibit hydrotropic behaviour. Hydrotrope aggregation is looser than the aggregation of surfactants, as micelles are not formed and the aggregation numbers are generally lower than those found in micelles. Finally, in contrast to surfactants, hydrotropes tend to be very selective in their ability to solubilise any particular solute.

In the present invention, the definition of hydrotropes is taken to mean a molecule consisting of a non-polar end and polar end, able to undergo pi-pi stacking or step-wise self-accumulation around the active agent but unable to form micelles, i.e. it is non-micellar, it does not form a bilayer. The non-micellar nature of hydrotropes is not related to concentration; unlike surfactants, hydrotropes will not form micelles at higher concentrations.

In the present invention, hydrotropes are used to modify the ability of active agents to enter and move through a mucosal membrane, not by using their ability to increase solubility and not by any increase in concentration gradient. Without being held to a theory, we understand that the invention uses the ability of hydrotropes to reduce the tendency of the active to be hindered by or bind to the lipid rich cellular membranes and/or lipid fractions and/or any other hydrophobic domains present in the intercellular space whilst maintaining or enhancing the ability of the active to pass through the lipid membranes to enter the oral mucosa.

Without going into detail on the many theories proposed for hydrotropic solubilisation of drugs, the interaction of the hydrotrope with the drug results in the reduction of the hydrophobic/lipophilic area exposed to the aqueous environment, resulting in a solubility enhancement in the aqueous environment. In some cases, interaction of the hydrotrope with the aqueous environment may add to the increased solubility. This reduction in hydrophobic character is shown when the normal octanol-water shake flask technique used to determine lipophilicity is applied to drug solutions containing hydrotropes. The drug partitions less into the octanol layer and more into the water layer in solutions containing hydrotropes.

However, the reduction in hydrophobic character results in greater solubility in water but reduced ability to penetrate and move through lipid membranes of the mouth, skin and intestines.

As discussed above, generally a hydrotrope is a molecule that is used to increase the solubility of an active agent, generally resulting in a concomitant decrease in membrane permeation. However, in the present invention the hydrotropes used are chosen to increase the penetration of the active agent into and through a membrane. The hydrotropes chosen may not, in fact, be able to increase the solubility, and may even in some cases decrease the solubility of that active agent.

The concentration increase due to addition of hydrotropes to increase solubility must be sufficiently high to create a very steep concentration gradient on the donor side of the membrane, in order to push the drug through the membrane against the repulsion from the lipophilic membrane towards the hydrophilic drug. The difference in the concentration of a molecule on one side of a membrane (donor side) versus the other is called a gradient; molecules are driven down their concentration gradients. A molecule's concentration gradient drives movement across the membrane until the molecule is at equilibrium. Movement from a high concentration to a low concentration is also referred to as movement "with" or "in the direction of" the concentration gradient or "downhill." Movement from a low concentration to a high concentration is also referred to as "against" the concentration gradient or "uphill." As the concentration equalises, there is no longer sufficient energy for the more hydrophilic hydrotrope complex to pass through the lipophilic membrane, "it is no longer going downhill" and no more drug is absorbed.

The use of hydrotropes to increase solubility of poorly water-soluble drugs usually results in a trade off against permeability, restricting potential increases in bioavailability. Beig et al (2013) *Oral Delivery of Lipophilic Drugs: The Tradeoff between Solubility Increase and Permeability Decrease When Using Cyclodextrin-Based Formulations.* PLoS ONE 8(7): e68237. modelled the solubility permeability interplay against experimental data in the context of the intestinal membrane. Significant increase in drug solubility (up to ~30 fold) with the addition of hydrotropes was offset by a concomitant permeability decrease in vitro and in vivo (up to ~17 fold) revealing a solubility-permeability trade-off when using hydrotropic drug solubilisation.

If the concentration of the drug on the donor side of a membrane is increased so much that the reduction in partition/permeability constant is overcome (with or without permeation enhancers reducing the lipophilic membrane barrier by reducing the ordered structure of the membrane), an increase in permeation (flux) through dermal, oral or intestinal mucosal membrane may occur.

In normal usage, the addition of hydrotropes to increase solubility increases the concentration of the drug on the donor side of the membrane, but concomitantly decreases the membrane permeability coefficient of the drug due to lowering of the partition coefficient (Log P) and/or distribution coefficient (Log D). The lowering of the coefficient Log P/Log D of the drug can be demonstrated in classical shake flask experiments. Traditionally, only when the concentration of the solubilised drug on the donor side of a membrane donor is sufficient to offset the decrease in permeability can the flux of drug be maintained or increased. However, the present invention does not work to this model.

Without being held to a theory, we believe that the loose complexation of the hydrotrope around the active agent molecule is sufficient to aid initial permeation of the more polar drugs into the mucosa and reduce the inhibitory effect of hydrophobic lipids and protein domains within the intercellular pathway. For more hydrophobic molecules, the hydrotrope aggregate acts as a shield against lipid or protein complexation and thus also enhances permeation. In effect, careful choice of hydrotrope matched with drug molecule results in an aggregate with more favourable lipophilicity for permeation through the oral mucosa.

The present invention surprisingly finds that addition of hydrotropes to drug compounds can result in an increase in flux in the absence of an increase in solubilised drug on the donor side of the membrane, in opposition to the observed norm. Contradictory to previous findings, the effect of the hydrotrope is to increase the membrane permeability coefficient with concomitant decrease in aqueous solubility.

The novel hydrotrope effect thus described does not require a concentration gradient, and is maintained throughout the permeation, even at low concentrations within the membrane. The hydrotrope aggregation is maintained within the membrane, modifying the lipophilic character of the drug so that it does not bind strongly with the lipid rafts present within the buccal mucosa or more structured lipid domains of other membranes.

This unexpected phenomenon has been shown capable of being extended to highly lipophilic compounds. Such compounds can easily migrate into membranes, but are retained within the membranes due to lipophilic interactions. The addition of hydrotropes according to the present invention results in a more favourable lipophilicity (i.e. the hydrotropes are altering the apparent log P/log D), allowing the highly lipophilic compounds to migrate in, through and out of the membrane.

We have utilised the ability of the hydrotrope to change the apparent log P/log D of the drug to produce the optimal lipophilicity for a compound to enter the membrane and permeate through, without becoming trapped within the membrane.

TABLE 1

Differences between hydrotropes and surfactants (from Narang & Mahato (Ed); *Targeted Delivery of Small and Macromolecular Active agents* [2010] page 524)

| Hydrotrope | Surfactant |
| --- | --- |
| High concentration to provide effect | Low effective concentration |
| Usually aromatic structure with ionisable groups (may have short lipid chain) | Usually aliphatic structure with polar head groups |
| Multiple mechanisms to induce hydrotropic active agent solubilisation | |
| Compound (active agent) selectivity | little selectivity |

Examples of suitable hydrotropes include, but are not limited to:

Aromatic alcohols e.g. catechol;
Naphthols;
Alkaloids e.g. caffeine, nicotinamide, nicotinamide derivatives;
Aliphatic acids and their salts;
Aromatic acids and their salts e.g. benzoates, salicylates;
Aromatics with anionic head groups;
Aromatics with cationic head groups; and
Ureas.

Examples of suitable hydrotropes include, but are not limited to: caffeine, nicotinamide and derivatives, sodium benzoate, ascorbic acid, sodium salicylate, benzoic acid, propyl paraben, citric acid, salicylic acid, benzoic acid, phenols and their corresponding salts, sodium alkyl, aryl and alkylaryl sulfonic acids (e.g. benzene, toluene, xylene, cumene, cymene) and their salts, sodium butyl glycol sulfate sodium acetate, sodium p-toluenesulfonate and sodium xylene sulfonate. FIG. 1 provides examples of some representative hydrotrope structures.

In relation to hydrotropy, the primary binding force for non-bonded complexation in aqueous solution is a decrease in the hydrophobic surface area in contact with the water surface area following complexation or aggregation.

In relation to the self-stacking model, the stacking of hydrotropes generally occurs such that the similar ends of the hydrotropes are separated, which leads to minimum repulsion of bond dipoles. In contrast, during the stacking of molecules with different structures, such as the hydrotrope and the active agent or two different hydrotropes, there may be different, more favourable, dipolar interactions.

In both cases, the hydrophobic surface area of the hydrotrope is a qualitative indicator of complexing ability, with the hydrotrope with the greater hydrophobic surface area being the better complexing agent, as it complexes better with the active agent or with other hydrotropes to reduce the hydrophobic surface area exposed to water. The log P of a hydrotrope is a good secondary indicator as far as given hydrophobic area; alternatively the hydrotrope with the higher log D is generally the better complexing agent. However, all of these factors (hydrophobic surface area, log P or log D) are simply indicators, the relationship is qualitative and is affected by many factors. There is no chemical structure or physical property that explains all hydrotropic interactions.

Higuchi and Kristiansen (*J Pharm Sci.* (1970) 59(11): 1601-8) proposed two large distinct classes of solutes including hydrotropes, based on experimental data on efficient binding between organic species dissolved in water. Although this theory was developed based on aqueous binding stability, without being held to the theory we believe that it may be applicable to increasing permeability of active agents by interaction with hydrotropes. Class A hydrotropic compounds contain uncharged aromatic nitrogen and conjugated cyclic amide groups and Class B hydrotropic compounds contain aromatic acids and aldehydes. Class A hydrotropes can transfer to Class B on ionisation.

According to the Biopharmaceutical Classification System (BCS), active agents are classified into four classes upon their solubility and permeability:

Class I—high permeability, high solubility: compounds are well absorbed and their absorption rate is usually higher than excretion.

Class II—high permeability, low solubility: bioavailability is limited by their solvation rate. A correlation between the in vivo bioavailability and the in vitro solvation can be found.

Class III—low permeability, high solubility: absorption is limited by the permeation rate but the compound is solvated very fast. Variability is often seen, but if the formulation does not change the permeability or gastrointestinal duration time, then class I criteria can be applied.

Class IV—low permeability, low solubility: poor bioavailability. Usually they are not well absorbed over the intestinal mucosa and a high variability is expected.

Examples are tabulated below with examples of active agents that show greatest modified permeability on complexation with that class of hydrotrope.

| CLASS A hydrotropes Uncharged aromatics and conjugates | CLASS B hydrotropes Charged aromatics and charged aliphatics |
|---|---|
| Alkylxanthines | Benzoic acid and salts |
| Caffeine | Salicylic acid and salts |
| Theophylline | Ferulic acid |
| Nicotinamide | Cinnamide cinnamates |
| Prednisolone | Phenacetin |
| | Promethazine |
| | Menadione |
| | Citric acid and salts |
| | Ascorbic acid and salts |
| | Acetates |
| Actives whose permeability is modified with Class A hydrotropes | Actives whose permeability is modified with Class B hydrotropes |
| Ondansetron HCl (logP 2.4 BCS III) | Zolpidem tartrate (logP 1.2 BCS I) |
| Sildenafil citrate (logP 1.9 BCS I) | Sumatriptan succinate (logP 0.93 BCS III) |
| Doxylamine succinate (logP 2.96 BCS I) | Diphenhydramine HCl (logP 3.65 BCS I) |
| Diclofenac sodium (logP 4.5 BCS II hydroalcoholic solution) | |

Experimental data indicates that, in general,

Class A hydrotropes modify the permeability of active agents with a log P above 1.5;

Class B hydrotropes modify the permeability of a wide range of active agents and the most effective hydrotrope can be can be modified by the addition of co-solvents and other solubility modulators;

both Class A and B hydrotropes modify the permeability of active agents of BCS Class I (high solubility drug classes with high permeability);

both Class A and B hydrotropes modify the permeability of active agents of BCS Class III (high solubility drug classes with low permeability).

Class A and B hydrotropes may have little effect on BCS Class II and IV active agents in aqueous solution without the addition of co-solvents or other solubilising agents (including hydrotropes used for that purpose) as there is insufficient solubilised active agent for the permeability modification to have a useful effect Generally, if two hydrotropes interact, the binding is stronger between a hydrotrope of Class A and a hydrotrope of Class B (rather than between two Class A hydrotropes). However, surprisingly the ability of a hydrotrope to increase permeability for a particular active does not seem to depend on the stronger binding seen between Class A and B type compounds. For example, ondansetron has many similarities to Class A hydrotropes but achieves the greatest increases in permeability with Class A hydrotropes (whereas binding might be thought to be highest between a Class B hydrotrope and a Class A type active). In one form of the invention, actives may be generalised into classes in the same manner to hydrotropes, with Class A actives containing uncharged aromatic nitrogen and conjugated cyclic amide groups and Class B actives containing aromatic acids and aldehydes. Class A actives can transfer to Class B on ionisation.

Permeability of drugs through the mucosal surface is dependent firstly on entry through the lipid membrane, and secondly by permeation through the mucosa. Some drugs may be readily absorbed, but then complex within the mucosa and have a slow rate of release into the blood system. Typically, drugs which complex with Class A hydrotropes to give improved permeability in the primary in vitro screen will not have early increased permeability due to binding in the mucosa. Drugs which show increased in vitro permeability with Class B screens in general will also show an increase in early bioavailability. Class A hydrotrope preferred drugs may have increased early bioavailability by the addition of Class B hydrotropes in a synergistic combination to provide the best bioavailability profile.

It is possible to manipulate the class of hydrotrope which gives in vitro permeation increase by the addition of co-solvents to the aqueous solution of the drug.

Preferably, the hydrotrope or hydrotropes are present in the composition at a total amount of less than 15% by weight of the composition. More preferably, the hydrotrope or hydrotropes are present in the composition at a total amount of less than 15% or 10% or less than by weight of the composition. The amount of hydrotrope or each of the hydrotropes may be 14%, 12%, 10%, 9%, 8%, 7%, 6%, 5%, 4%, 3%, 2%, 1%, 0.5% or 0.25%. For example, if two hydrotropes are used, there may be 2.5% of hydrotrope X and 7.5% of hydrotrope Y. If a higher amount of hydrotrope (i.e. above 10%) is used, the additional hydrotrope is not present to increase solubility, but rather to provide a more cohesive or thicker barrier between the active agent and the surrounding environment via stacking or self-accumulation. The active is completely solubilised at the required dosage concentration, before the permeation enhancing hydrotrope is added. The hydrotrope or hydrotropes may be present in the composition at a total amount of less than 14%, 12%, 10%, 9%, 8%, 7%, 6%, 5%, 4%, 3%, 2%, 1%, 0.5% or 0.25%.

An amount of hydrotrope added is such that there is no improvement in solubility, but there is an increase in permeability. For example, a bulk solution of the active agent may be divided into portions and individual hydrotropes added to each portion bar the control. The solutions thus contain the exact same concentration of active agent in the presence or absence of hydrotrope. The samples may then be tested for permeability through an artificial membrane under identical conditions so that the effect of the hydrotrope on the permeability of the active can be assessed.

The use of low amounts (less than 15%, preferably 10% or less) of hydrotropes assists in taking advantage of their ability to enhance the penetration by an active agent of a mucosal membrane by complexing and effectively enclosing the active agent and allowing the active to travel through the intercellular space with minimal interaction with the lipids or other hydrophobic domains present there, without taking advantage of some hydrotropes' ability to increase the solubility of some actives. The hydrotropes may also interact with the membranes of the mucosal cells, which may contribute to the increase in permeability of more hydrophilic compounds (log P or log D less than 1.0), as any disruption of the membranes via hydrotropic action will allow greater partitioning of the active agent into the mucosa and also open up the intercellular spaces to the more hydrophilic compounds.

Without being held to a theory, we believe that the presence of hydrotropes allows the active agents to move through the intercellular space with reduced or absent hindrance from or binding to the lipid rich cellular membranes and/or lipid fractions and/or any other hydrophobic domains present in the intercellular space. This movement is facilitated by the hydrotrope participating in parallel self-stacking (pi-pi stacking) complexation around the active agent and/or non-stoichiometric self-accumulation around the active agent. This stacking and/or self-accumulation reduces the exposure of the active agent to lipids in cellular membranes and lipid fractions present in the intercellular space, and permits the active agent to move freely through the intercellular space.

The present invention does not rely on the ability of hydrotropes to increase the solubility of active agents. There is generally a minimum hydrotrope concentration (MHC) necessary for increased solubilisation to occur. Relatively high levels of hydrotrope are required to reach MHC, and the present invention generally uses hydrotropes at less than the MHC.

The present invention does not rely on the ability of certain hydrotropes to lyse cell walls at high concentration and applied volume.

The present invention does not rely on any particular characteristic of the hydrotropes; rather the hydrotrope is matched to the active agent to provide a favourable complex by stacking or self-accumulating. The amount of hydrotrope required is lower than that usually used to increase solubility and less than that used to extract compounds through cell membranes Hydrotropes may be matched to specific drug molecules through a screening process and the effects on mucosal permeability assessed via an initial artificial membrane, then ex vivo porcine buccal tissue membrane on standard Franz cells using a base formulation without hydrotropes as the comparator. The base formulation should always have the same concentration of API as the hydrotrope variants, so it is clear there is no influence on permeation from concentration differences.

The hydrotropes are present at concentrations where there is minimal or no damage to the cell membranes and generally below minimum hydrotrope concentration levels required for increased solubilisation of the drug.

Active agents with high lipophilicity (log P or log D greater than 3.5) penetrate easily into the intercellular spaces between the mucosal membrane cells and they do not bind strongly to the polar lipids in those intercellular spaces. Highly lipophilic active agents in oil solvent formulations will pass through the intercellular spaces of the mucosa freely and may indeed show retarded permeation with application of hydrotropes. However, lipophilic active agents in more polar solvent formulations will benefit from hydrotrope-active agent stacking or self-accumulation in order to reduce complexation with intercellular lipids and cell membranes during movement through the intercellular spaces.

Active agents of intermediate lipophilicity (log P or log D between 1.0 and 3.5) can normally penetrate the intercellular spaces between the mucosal membrane cells. Active agents with a log P of between 1.0 and 3.5 may be quickly absorbed but often have slow permeability across mucosal membranes. Due to their less lipophilic nature, they may interact with the polar lipids of cell membranes and lipid fractions in the intercellular space, which results in the impedance of progress. It is postulated that the hydrotropes prevent or reduce this interaction and facilitate the passage of intermediate lipophilicity active agents through the polar regions of the intercellular matrix by the stacking or self-accumulation of the hydrotrope around the active agent, resulting in an increase in the speed and amount of active agent moving through the intercellular space and being absorbed into plasma. The presence of the hydrotrope masks the active agent and prevents binding of the agent to the lipid rich cellular membranes and/or lipid lamellae fractions present in the intercellular space.

Compounds of low lipophilicity (log P or log D less than 1.0) may be aided in entry into the intercellular spaces between the mucosal membrane cells by the ability of the hydrotrope to stack or self-self-accumulate around the active agent and also to disrupt the surface membrane of the mucosal cells by interaction with the lipid membrane. Lipids within the intercellular spaces can act as a major hindrance to the more hydrophilic compounds. It is postulated that the hydrotropes facilitate passage by shielding the hydrophilic active agents from interaction with the polar lipids within the intercellular spaces via stacking or self-accumulation, and also by opening up the intercellular spaces through disrupting the lipids of the cell membranes.

Careful manipulation of concentrations and mixtures of hydrotropes can be used to deliver fast permeation (leading to immediate release into the bloodstream), or slow permeation (leading to sustained release into the bloodstream).

Examples of suitable active agents include, but are not limited to: sildenafil (log P 1.9), tadalafil (log P 1.7), sumatriptan (log P 0.93), zolpidem (log P 1.2), ondansetron (log P 2.4), and midazolam (log P 3.3). Other agents include oestradiol, ibuprofen, nifedipine, nitroglycerine, nicotine, propanalol, almotriptan, zolmetriptan, rizatripan, neratriptan, lorazepam and diazepam.

Salts of suitable active agents may be better described by log D under controlled pH conditions. For example sildenafil citrate (log D 1.6, pH 7), sumatriptan succinate (log D 1.7, pH 6). In the present invention, the skilled reader will understand which term selected from partition co-efficient (log P) or distribution coefficient (log D) is more appropriate for the particular situation.

FIG. 2 provides examples of some representative active agent structures for compounds with partition co-efficient (log P) or distribution coefficient (log D) between 0 and 5.

In relation to the active agents, the log P or log D is preferably greater than 0, greater than 0.5, or more preferably greater than 0.9. The log P or log D is furthermore preferably less than 5.0, more preferably less than 3.5. Therefore, the log P or log D is preferably between 0 and 5, or between 0.5 and 3.5, 0.9 and 5 or 0.9 and 3.5. More preferably, the log P or log D is between 1.0 and 3.5. The log P or log D may be between 1 and 5, 1 and 3, 2 and 4, or 2.5 and 3.5. The log P or log D of the active agents may be 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 or 5.0.

With reference to the possible mechanism of hydrotrope activity discussed above, if hydrotropes complex with the active agent by parallel self-stacking complexation, then at least part of the active agent should be planar. However, if the hydrotropes carry out non-stoichiometric self-self-accumulation around the active agent, no planarity is required.

The present invention therefore provides a composition comprising:

a) one or more hydrotropes in a total amount of less than 15% by weight of the composition; and
b) an active agent with a log P or log D of between 0 and 5.

The present invention further provides a composition comprising:

a) one or more hydrotropes that are able to self-self-accumulate but unable to form micelles in a total amount of less than 15% by weight of the composition; and
b) an active agent with a log P or log D of between 0 and 5.

The present invention further provides a composition comprising:

a) one or more hydrotropes in a total amount of less than 15% by weight of the composition; and
b) an active agent with a log P or log D of between 0 and 5.

Preferably, the active agent has a log P or log D of between 0.9 and 3.5, more preferably between 2.5 and 3.5, most preferably between 0.5 and 3.0. The active agent may have a log P or log D of greater than 3.5, between 1.0 and 3.5 or less than 1.0.

Preferably the log P or log D of the active agents is between 0 and 5.0 and the hydrotropes are present in a total amount of less than 15% by weight of the composition, or the log P or log D of the active agents is between 0 and 5.0 and the hydrotropes are present in a total amount of less than 12% by weight of the composition. More preferably, the log P or log D of the active agents is between 0 and 5.0 and the hydrotropes are present in a total amount of less than 10% by weight of the composition.

Preferably the log P or log D of the active agents is between 0.9 and 3.5 and the hydrotropes are present in a total amount of less than 15% by weight of the composition, or the log P or log D of the active agents is between 0.9 and 3.5 and the hydrotropes are present in a total amount of less than 12% by weight of the composition. More preferably, the log P or log D of the active agents is between 0.9 and 3.5 and the hydrotropes are present in a total amount of less than 10% by weight of the composition.

Preferably the log P or log D of the active agents is between 2.5 and 3.5 and the hydrotropes are present in a total amount of less than 15% by weight of the composition, or the log P or log D of the active agents is between 2.5 and 3.5 and the hydrotropes are present in a total amount of less than 12% by weight of the composition. More preferably, the log P or log D of the active agents is between 2.5 and 3.5 and the hydrotropes are present in a total amount of less than 10% by weight of the composition.

Preferably the log P or log D of the active agents is between 1.0 and 3.5 and the hydrotropes are present in a total amount of less than 15% by weight of the composition, or the log P or log D of the active agents is between 1.1 and 3.5 and the hydrotropes are present in a total amount of less than 12% by weight of the composition. More preferably, the log P or log D of the active agents is between 1.1 and 3.5 and the hydrotropes are present in a total amount of less than 10% by weight of the composition.

The compositions of the present invention may optionally comprise a non-hydrotrope co-solvent. The hydrotropes of the present invention, although sometimes used as solvents at high concentrations for some compounds, may not be themselves particularly soluble in an aqueous (water) environment. Therefore, a co-solvent may be added to the hydrotrope prior to mixing with the active agent, in order to increase the solubility of the hydrotrope. The hydrotrope is then able to undergo stacking complexation and/or self-accumulation and interact with the active agent.

Alternatively, the hydrotrope may require the presence of a co-solvent to stabilise the hydrotrope in solution and thus allow the process of stacking complexation and/or self-accumulation to occur.

Preferably the co-solvent solubilises both API and hydrotrope. The active and hydrotrope may be in a solution with no aqueous components, and simply be composed of one or more other solvents. The solvent or solvent:co-solvent combination should have a suitable dielectric constant to solubilise both the active agent and the hydrotrope.

Examples of suitable co-solvents include, but are not limited to: aliphatic alcohols e.g. ethanol; glycols e.g. PPG, PEG; glycerine; and any other pharmaceutically acceptable co-solvent known to those skilled in the art.

The present invention therefore provides a composition comprising:
a) one or more hydrotropes in a total amount of less than 15% by weight of the composition;
b) an active agent with a log P or log D of greater than 2.5; and
c) a co-solvent.

The invention provides a method to increase the penetration of active agents through mucosal membranes, the method comprising the step of:
a) administering to a subject in need a composition comprising:
i) one or more hydrotropes in a total amount of less than 15% by weight of the composition; and
ii) an active agent with a log P or log D of between 0 and 5.

The invention also provides a method to increase the penetration of active agents through mucosal membranes, the method comprising the step of:
a) administering to a subject in need a composition comprising:
i) one or more hydrotropes in a total amount of less than 15% by weight of the composition;
ii) an active agent with a log P or log D of between 0 and 5; and
iii) a co-solvent.

The present invention provides a kit containing:
a) one or more hydrotropes in a total amount of less than 15% by weight of the composition;
b) an active agent with a log P or log D of between 0 and 5; and
c) instructions for use.

The present invention also provides a kit containing:
a) one or more hydrotropes in a total amount of less than 15% by weight of the composition;
b) an active agent with a log P or log D of between 0 and 5;
c) a co-solvent; and
d) instructions for use. Preferably the log P or log D of the active agents is between 0 and 5 and the hydrotropes are present in a total amount of less than 15% by weight of the composition, or the log P or log D of the active agents is between 0 and 5 and the hydrotropes are present in a total amount of less than 12% by weight of the composition. More preferably, the log P or log D of the active agents is between 0 and 5 and the hydrotropes are present in a total amount of less than 10% by weight of the composition.

Preferably the log P or log D of the active agents is between 0.9 and 3.5 and the hydrotropes are present in a total amount of less than 15% by weight of the composition, or the log P or log D of the active agents is between 0.9 and 3.5 and the hydrotropes are present in a total amount of less than 12% by weight of the composition. More preferably, the log P or log D of the active agents is between 0.9 and 3.5 and the hydrotropes are present in a total amount of less than 10% by weight of the composition.

Preferably the log P or log D of the active agents is between 2.5 and 3.5 and the hydrotropes are present in a total amount of less than 15% by weight of the composition, or the log P or log D of the active agents is between 2.5 and 3.5 and the hydrotropes are present in a total amount of less than 12% by weight of the composition. More preferably, the log P or log D of the active agents is between 2.5 and 3.5 and the hydrotropes are present in a total amount of less than 10% by weight of the composition.

Preferably the log P or log D of the active agents is between 0.5 and 3.0 and the hydrotropes are present in a total amount of less than 15% by weight of the composition, or the log P or log D of the active agents is between 0.5 and 3.0 and the hydrotropes are present in a total amount of less than 12% by weight of the composition. More preferably, the log P or log D of the active agents is between 0.5 and 3.0 and the hydrotropes are present in a total amount of less than 10% by weight of the composition.

The invention provides a therapeutic composition comprising:
a) one or more hydrotropes in a total amount of less than 15% by weight of the composition;
b) an active agent with a log P or log D of between 0 and 5; and
c) pharmaceutically acceptable excipients.

The invention also provides a therapeutic compositions comprising:
a) one or more hydrotropes in a total amount of less than 15% by weight of the composition;
b) an active agent with a log P or log D of between 0 and 5;
c) a co-solvent; and
d) pharmaceutically acceptable excipients.

Preferably the log P or log D of the active agents is between 0 and 5 and the hydrotropes are present in a total amount of less than 15% by weight of the composition, or the log P or log D of the active agents is between 0 and 5 and the hydrotropes are present in a total amount of less than 12% by weight of the composition. More preferably, the log P or log D of the active agents is between 0 and 5 and the hydrotropes are present in a total amount of less than 10% by weight of the composition.

Preferably the log P or log D of the active agents is between 0.9 and 3.5 and the hydrotropes are present in a total amount of less than 15% by weight of the composition, or the log P or log D of the active agents is between 0.9 and 3.5 and the hydrotropes are present in a total amount of less than 12% by weight of the composition. More preferably, the log P or log D of the active agents is between 0.9 and 3.5 and the hydrotropes are present in a total amount of less than 10% by weight of the composition.

Preferably the log P or log D of the active agents is between 2.5 and 3.5 and the hydrotropes are present in a total amount of less than 15% by weight of the composition, or the log P or log D of the active agents is between 2.5 and 3.5 and the hydrotropes are present in a total amount of less than 12% by weight of the composition. More preferably, the log P or log D of the active agents is between 2.5 and 3.5 and the hydrotropes are present in a total amount of less than 10% by weight of the composition.

Preferably the log P or log D of the active agents is between 0.5 and 3.0 and the hydrotropes are present in a total amount of less than 15% by weight of the composition, or the log P or log D of the active agents is between 0.5 and 3.0 and the hydrotropes are present in a total amount of less than 12% by weight of the composition. More preferably, the log P or log D of the active agents is between 0.5 and 3.0 and the hydrotropes are present in a total amount of less than 10% by weight of the composition.

The composition may further comprise carriers, excipients and/or diluents. Generally, examples of suitable carriers, excipients and diluents include, without limitation, water, saline, ethanol, dextrose, glycerol, lactose, dextrose, sucrose, sorbitol, mannitol, starches, gum acacia, calcium phosphates, alginate, tragacanth, gelatine, calcium silicate, microcrystalline cellulose, polyvinylpyrrolidone, cellulose, water syrup, methyl cellulose, methyl and propylhydroxybenzoates, polysorbates, talc magnesium stearate, mineral oil or combinations thereof. The compositions can additionally include lubricating agents, pH buffering agents, wetting agents, emulsifying and suspending agents, preserving agents, sweetening agents or flavouring agents.

Dosage and route of administration should be determined by the nature of the active gents and the specific condition of the patient and be selected accordingly. Preferred types of pharmaceutical compositions are, for example, oral, parenteral, enteral, intravenous, suppository, intraperitoneal, topical, transdermal (e.g., using any standard patch), ophthalmic, nasally, local, non-oral, such as aerosol, inhalation, subcutaneous, intramuscular, buccal, sublingual, rectal, vaginal, intra-arterial, and intrathecal, etc. They can be administered alone, or in combination with any ingredient(s), active or inactive. The preferred route of administration is transdermal, sublingual, buccal, vaginal, rectal or aerosol.

The composition can contain from 0.1% to 99% by weight, preferably 10% by weight-90% by weight, of each of the active agents. If the compositions contain dosage units, each unit preferably contains from 50 mg to 4 g of each active agent.

The composition may be administered one a day, twice a day, three times a day or more often. Alternatively, the composition may be administered weekly, monthly etc, particularly if the composition is administered in the form of a slow release dosage. The choice of dosage administration timing is reliant on factors such as the route of administration (e.g. oral, parenteral, topical, infusion etc), the release rate of the dosage (e.g. slow release, rapid release), the nature of the condition being treated and/or the subject being administered the dosage. Each of these factors will be taken into consideration when designing a dosage regime.

Topical Compositions

The pharmaceutical composition may be adapted for topical application. In this regard, various topical delivery systems may be appropriate for administering the compositions of the present invention depending up on the preferred treatment regimen. Topical compositions may be produced by dissolving or combining the active agents and hydrotropes of the present invention in an aqueous or non-aqueous carrier. In general, any liquid, cream, or gel or similar substance that does not appreciably react with the compound or any other of the active ingredients that may be introduced into the composition and which is non-irritating is suitable. Appropriate non-sprayable viscous, semi-solid or solid forms can also be employed that include a carrier compatible with topical application and have dynamic viscosity preferably greater than water.

Suitable compositions are well known to those skilled in the art and include, but are not limited to, solutions, suspensions, emulsions, creams, gels, ointments, powders, liniments, salves, aerosols, transdermal patches, etc, which are, if desired, sterilised or mixed with auxiliary agents, e.g. preservatives, stabilisers, emulsifiers, wetting agents, fragrances, colouring agents, odour controllers, thickeners such as natural gums, etc. Particularly preferred topical compositions include ointments, creams or gels.

Ointments generally are prepared using either (1) an oleaginous base, i.e., one consisting of fixed oils or hydrocarbons, such as white petroleum, mineral oil, or (2) an absorbent base, i.e., one consisting of an anhydrous substance or substances which can absorb water, for example anhydrous lanolin. Customarily, following formation of the base, whether oleaginous or absorbent, the active agents and hydrotropes are added to an amount affording the desired concentration.

Creams are oil/water emulsions. They consist of an oil phase (internal phase), comprising typically fixed oils, hydrocarbons and the like, waxes, petroleum, mineral oil and the like and an aqueous phase (continuous phase), comprising water and any water-soluble substances, such as added salts. The two phases are stabilised by use of an emulsifying agent, for example, a surface active agent, such as sodium lauryl sulfite; hydrophilic colloids, such as acacia colloidal clays, veegum and the like. Upon formation of the emulsion, the active agents and hydrotropes can be added in an amount to achieve the desired concentration.

Gels comprise a base selected from an oleaginous base, water, or an emulsion-suspension base. To the base is added a gelling agent that forms a matrix in the base, increasing its viscosity. Examples of gelling agents are hydroxypropyl cellulose, acrylic acid polymers and the like. Customarily, the active agents and hydrotropes are added to the composition at the desired concentration at a point preceding addition of the gelling agent.

The amount of active agents and hydrotropes incorporated into a topical composition is not critical; the concentration should be within a range sufficient to permit ready application of the composition such that an effective amount of the active agents and hydrotropes is delivered.

Aerosols

Pharmaceutical compositions are also provided which are suitable for administration as an aerosol, by inhalation. These compositions comprise a solution or suspension of the active agents and hydrotropes or a plurality of solid particles of the active agents and hydrotropes. The desired composition may be placed in a small chamber and nebulized. Nebulization may be accomplished by compressed air or by ultrasonic energy to form a plurality of liquid droplets or solid particles comprising the active agents and hydrotropes.

The solid particles can be obtained by processing solid active agents and hydrotropes, in any appropriate manner known in the art, such as by micronization. Commercial nebulizers are also available to provide liquid droplets of any desired size.

The liquid droplets or solid particles for oromucosal absorption should have a particle size in the range of about 10 to about 120 microns, preferably from about 30 to about 80 microns. Most preferably, the size of the solid particles or droplets will be from about 30 to about 60 microns. Such particles or droplets may be dispensed by commercially available sprays or nebulisers or by other means known to the skilled person.

The liquid droplets or solid particles applications other than oromucosal delivery should have a particle size in the range of about 0.5 to about 5 microns, preferably from about 1 to about 2 microns. Most preferably, the size of the solid particles or droplets will be from about 1 to about 2 microns. Such particles or droplets may be dispensed by commercially available sprays or nebulisers or by other means known to the skilled person.

When the pharmaceutical composition suitable for administration as an aerosol is in the form of a liquid, the composition will comprise a water-soluble form of the active agents and hydrotropes, in a carrier that comprises water. The presence of a co-solvent may aid in the regard. A surfactant may be present which lowers the surface tension of the composition sufficiently to result in the formation of droplets within the desired size range when subjected to nebulization.

In addition, the pharmaceutical composition may also include other agents. For example, preservatives, surfactants, oils, humectants, emollients, chelating agents, dyestuffs, stabilizers or antioxidants may be employed. Water soluble preservatives that may be employed include, but are not limited to, benzalkonium chloride, chlorobutanol, thimerosal, sodium bisulfate, phenylmercuric acetate, phenylmercuric nitrate, ethyl alcohol, methylparaben, polyvinyl alcohol, benzyl alcohol and phenylethyl alcohol. The surfactant may preferably be polysorbate 80. Other suitable additives include lubricants and slip agents, such as, for example, magnesium stearate, stearic acid, talc and bentonites, substances which promote disintegration, such as starch or cross linked polyvinylpyrrolidone, binders, such as, for example, starch, gelatin or linear polyvinylpyrrolidone, and dry binders, such as microcrystalline cellulose.

Other vehicles that may be used include, but are not limited to, polyvinyl alcohol, povidone, hydroxypropyl methyl cellulose, poloxamers, carboxymethyl cellulose, hydroxyethyl cellulose, purified water, etc. Tonicity adjustors may be included, for example, sodium chloride, potassium chloride, mannitol, glycerin, etc. Antioxidants include, but are not limited to, sodium metabisulfite, sodium thiosulfate, acetylcysteine, butylatedhydroxyanisole, butylated hydroxytoluene, etc. The indications, effective doses, compositions, contraindications, vendors etc, of the active agents and hydrotropes in the compositions are available or are known to one skilled in the art. These active agents and hydrotropes may be present in individual amounts of from about 0.001% to about 5% by weight and preferably about 0.01% to about 2%.

Electrolytes such as, but not limited to, sodium chloride and potassium chloride may also be included in the composition.

Further, the compositions may contain microbial preservatives. Useful microbial preservatives include methylparaben, propylparaben, benzyl alcohol, phenoxyethanol and hydroxyacetophenone. The microbial preservative is typically employed when the composition is placed in a vial designed for multidose use.

Excipients which may be used are all the physiologically acceptable solid inert substances, either inorganic or organic in nature. Inorganic substances are, for example, sodium chloride, carbonates, such as calcium carbonate, bicarbonates, aluminium oxides, silicic acids, aluminas, precipitated or colloidal silicon dioxide and phosphates. Organic substances are, for example, sugars, cellulose, foodstuffs and feedstuffs, such as milk powder, animal flours, cereal flours and shredded cereals and starches.

Finally, it will be appreciated that the compositions of the present invention may comprise a plurality of active agents and/or hydrotropes as described herein.

The pharmaceutical composition may be formulated with, but not limited to, pharmaceutically acceptable carriers or diluents, fillers, polymers, glidants, and lubricants.

Suitable pharmaceutically acceptable carriers include, but are not limited to, water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, white paraffin, glycerol, alginates, hyaluronic acid, collagen, perfume oil, fatty acid monoglycerides and diglycerides, pentaerythritol fatty acid esters, hydroxy methylcellulose, and polyvinyl pyrrolidone. The carrier may also comprise any of the substances described in Remington: The Science and Practice of Pharmacy (Gennaro and Gennaro, Eds, 20th edition, Lippincott Williams & Wilkins, 2000); Theory and Practice of Industrial Pharmacy ((Lachman et al., eds., 3.sup.rd edition, Lippincott Williams & Wilkins, 1986); Encyclopedia of Pharmaceutical Technology (Swarbrick and Boylan, eds., 2nd edition, Marcel Dekker, 2002).

The fillers can be chosen from, but are not limited to, powdered cellulose, sorbitol, mannitol, various types of lactose, phosphates and the like.

The polymers can be chosen from, but not limited to, hydrophilic or hydrophobic polymers such as derivatives of cellulose (for example methylcellulose, hydroxypropyl cellulose, hypromellose, ethylcellulose); polyvinylpirolidone (for example povidone, crospovidone, copovidone); polymethacrylates (for example Eudragit RS, RL); lypophillic components (for example glyceryl monostearate, glyceryl behenate); and various other substances such as for example hydroxypropyl starch, polyethylene oxide, carrageenan and the like. Most commonly, hydrophilic swelling polymers of suitable viscosity such as hypromellose are used, preferably in amounts above 5%, and more preferably above 8%.

Glidants can be chosen from, but not limited to, colloidal silicon dioxide, talc, magnesium stearate, calcium stearate, aluminium stearate, palmitic acid, stearic acid, stearol, cetanol, polyethylene glycol and the like.

Lubricants can be chosen from, but not limited to, stearic acid, magnesium stearate, calcium stearate, aluminium stearate, sodium stearyl fumarate, talc, hydrogenated castor oil, polyethylene glycols and the like.

One of ordinary skill in the art will appreciate that the individual components of the present invention may change depending on the physical and chemical qualities needed for the pharmaceutical compositions in a given process and/or application to which the pharmaceutical compositions will be applied.

The present invention provides a method to manufacture a medicament composition for the delivery of an active agent with a log P or log D of between 0 and 5 to a subject in need thereof, in combination with one or more hydrotropes in a total amount of less than 15% by weight of the composition.

The present invention provides for the use of one or more hydrotropes in a total amount of less than 15% by weight of the composition for the manufacture of a medicament composition for the delivery of an active agent with a log P or log D of between 0 and 5 to a subject in need thereof.

Preferably the log P or log D of the active agents is between 0 and 5 and the hydrotropes are present in a total amount of less than 15% by weight of the composition, or the log P or log D of the active agents is between 0 and 5 and the hydrotropes are present in a total amount of less than 12% by weight of the composition. More preferably, the log P or log D of the active agents is between 0 and 5 and the hydrotropes are present in a total amount of less than 10% by weight of the composition.

Preferably the log P or log D of the active agents is between 0.9 and 3.5 and the hydrotropes are present in a total amount of less than 15% by weight of the composition, or the log P or log D of the active agents is between 0.9 and 3.5 and the hydrotropes are present in a total amount of less than 12% by weight of the composition. More preferably, the log P or log D of the active agents is between 0.9 and 3.5 and the hydrotropes are present in a total amount of less than 10% by weight of the composition.

Preferably the log P or log D of the active agents is between 2.5 and 3.5 and the hydrotropes are present in a total amount of less than 15% by weight of the composition, or the log P or log D of the active agents is between 2.5 and 3.5 and the hydrotropes are present in a total amount of less than 12% by weight of the composition. More preferably, the log P or log D of the active agents is between 2.5 and 3.5 and the hydrotropes are present in a total amount of less than 10% by weight of the composition.

Preferably the log P or log D of the active agents is between 0.5 and 3.0 and the hydrotropes are present in a total amount of less than 15% by weight of the composition, or the log P or log D of the active agents is between 0.5 and 3.0 and the hydrotropes are present in a total amount of less than 12% by weight of the composition. More preferably, the log P or log D of the active agents is between 0.5 and 3.0 and the hydrotropes are present in a total amount of less than 10% by weight of the composition.

General

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in the specification, individually or collectively and any and all combinations or any two or more of the steps or features.

The present invention is not to be limited in scope by the specific embodiments described herein, which are intended for the purpose of exemplification only. Functionally equivalent products, compositions and methods are clearly within the scope of the invention as described herein.

The entire disclosures of all publications (including patents, patent applications, journal articles, laboratory manuals, books, or other documents) cited herein are hereby incorporated by reference. No admission is made that any of the references constitute prior art or are part of the common general knowledge of those working in the field to which this invention relates.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

As used herein the term "derived" and "derived from" shall be taken to indicate that a specific integer may be obtained from a particular source albeit not necessarily directly from that source.

As used herein, the singular forms "a," "an" and "the" include plural references unless the context clearly dictates otherwise.

Throughout this specification, unless the context requires otherwise, the word "comprise", or variations such as "comprises" or "comprising", will be understood to imply the inclusion of a stated integer or group of integers but not the exclusion of any other integer or group of integers.

Other than in the operating example, or where otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the specification and claims are approximations that may vary depending upon the desired properties sought to be obtained by the present invention. Hence "about 80%" means "about 80%" and also "80%". At the very least, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value; however, inherently contains certain errors necessarily resulting from the standard deviation found in their respective testing measurements Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

The following examples serve to more fully describe the manner of using the above-described invention, as well as to set forth the best modes contemplated for carrying out various aspects of the invention. It is understood that these methods in no way serve to limit the true scope of this invention, but rather are presented for illustrative purposes.

EXAMPLES

Example 1

In Vitro Single Hydrotrope Permeability Experiments—Coated Artificial Membranes

Regenerated cellulose membrane filters are coated with lecithin in dodecane for permeation experiments. Filters are prepared by pipetting 1 mL of 20% Lecithin on to a filter placed on a Franz cell receiver chamber filled with PBS at a pH optimised for permeant solubility and containing micro-stirring bar. Air bubbles are removed before donor chamber is clamped. The filter is incubated for 1 h and any excess lecithin solution is then removed. All samples are continuously stirred on a magnetic plate at 300 rpm for duration of pre-incubation and subsequent permeation experiment.

After membrane preparation and equilibration, 240 uL each of formulation at buffer pH 6.8 are added to the donor chamber.

The drugs reach equilibrium between the donor and acceptor chamber within 20-30 minutes and, as this is passive diffusion, the concentrations begin to fluctuate as equilibria are obtained and some back flow into the donor chamber may occur.

TABLE 2

Example Formulations

| Materials | Content (single hydrotrope) |
|---|---|
| Active Pharmaceutical Ingredient | 1-15% |
| Ascorbic acid and salts | 0.1-10% |
| Citric acid and salts | 0.1-10% |
| Benzoic acid and salts | 0.05-5% |
| Salicylic acid and salts | 0.05-5% |
| Sodium acetate | 0.05-5% |
| Parabens | 0.05-0.4% |
| Caffeine | 0.1-10% |
| Nicotinamide and substituted derivatives | 0.05-10% |

Hydrotropes may then be mixed as certain combinations which act synergistically bringing to a maximum total hydrotrope content to not more than 15%

TABLE 3

Some typical Hydrotrope concentrations in formulations

| Hydrotrope | Concentration | molwt | mMol/L |
|---|---|---|---|
| Ascorbic acid | 0.3% | 176 | 17.0 |
| Benzoic acid | 0.5% | 122 | 41.0 |
| Sodium benzoate | 0.05% (Sumatriptan only) | 144 | 3.5 |
| Sodium benzoate | 0.5% | 144 | 34.7 |
| Caffeine | 0.5% | 194 | 25.8 |
| Caffeine | 2.5% | 194 | 128.9 |
| Citric acid monohydrate | 0.1% | 192 | 5.2 |
| Nicotinamide | 0.05% | 122 | 4.1 |
| Nicotinamide | 7.5% | 122 | 614.8 |
| Sodium citrate | 0.1% | 258 | 3.9 |
| Propyl paraben | 0.005% | 180 | 0.3 |
| Sodium acetate | 0.05% | 82 | 6.1 |

Figure 3:
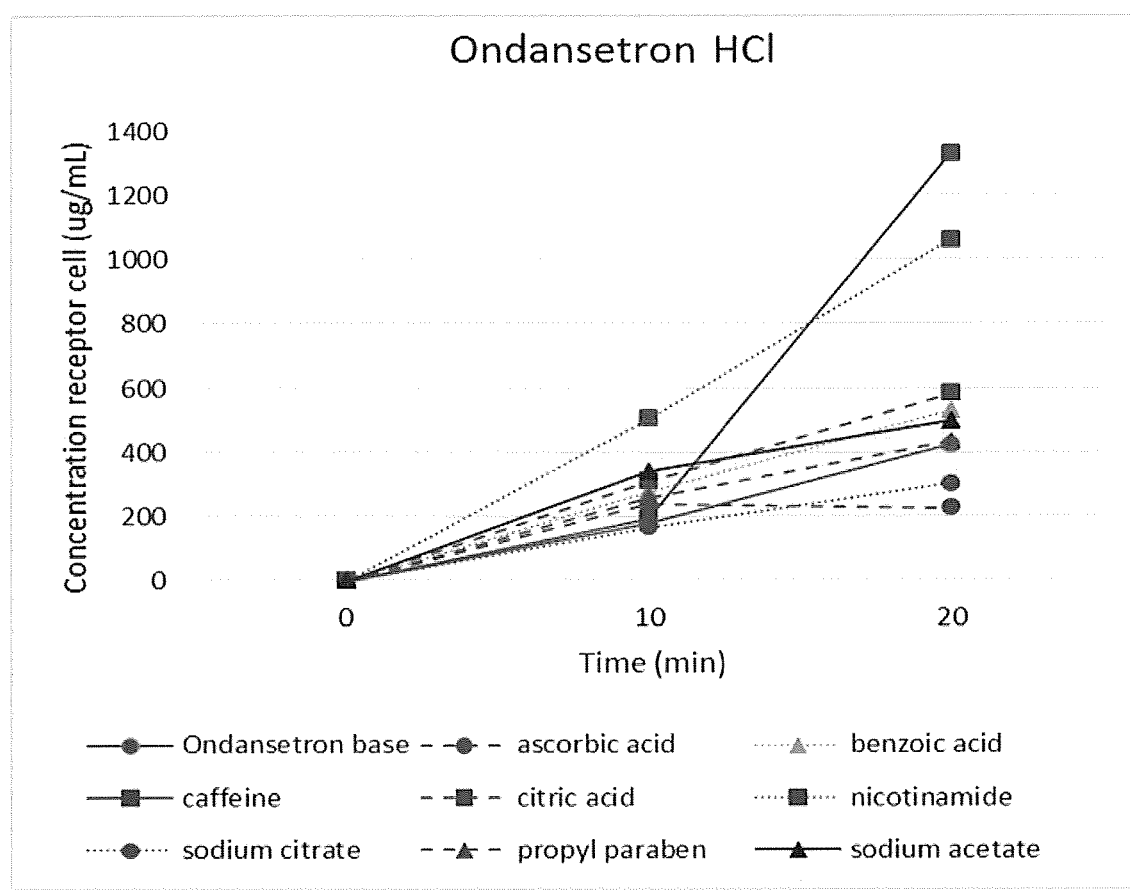
FIG. 3 is a graph of the penetration of ondansetron hydrochloride through an artificial membrane in the presence of various hydrotropes.
Figure 4:
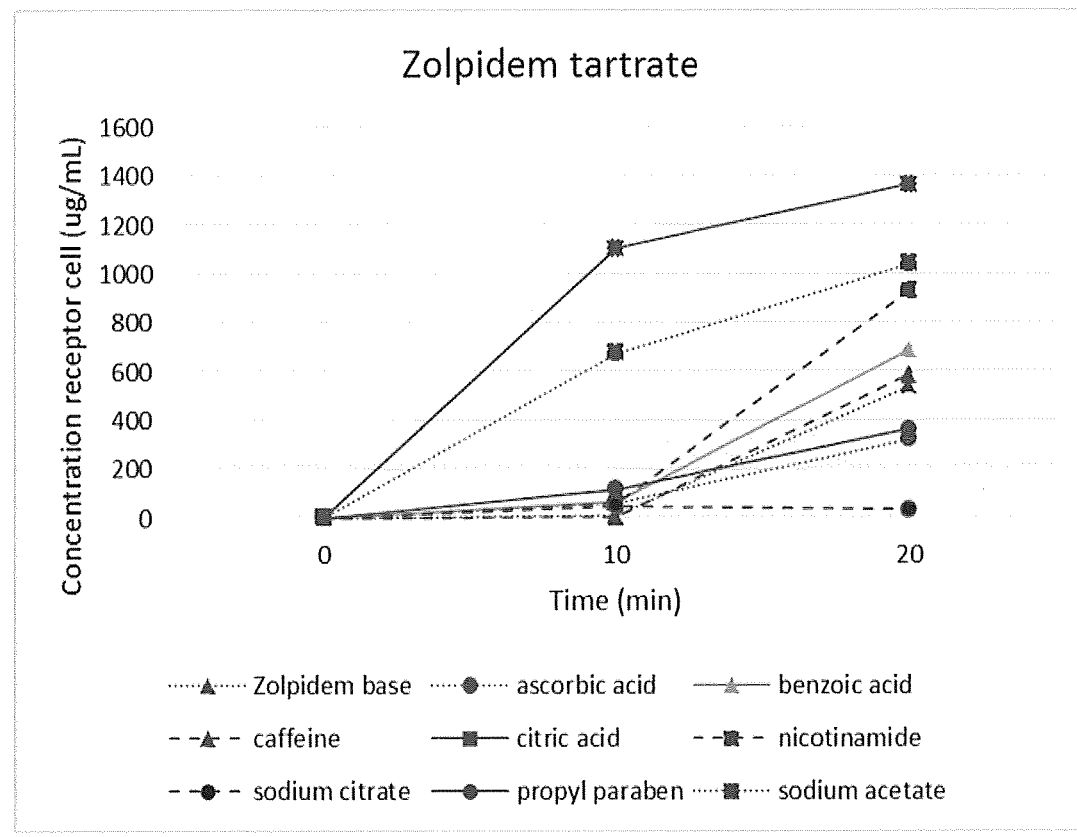
FIG. 4 is a graph of the penetration of zolpidem tartrate through an artificial membrane in the presence of various hydrotropes.
Figure 5:
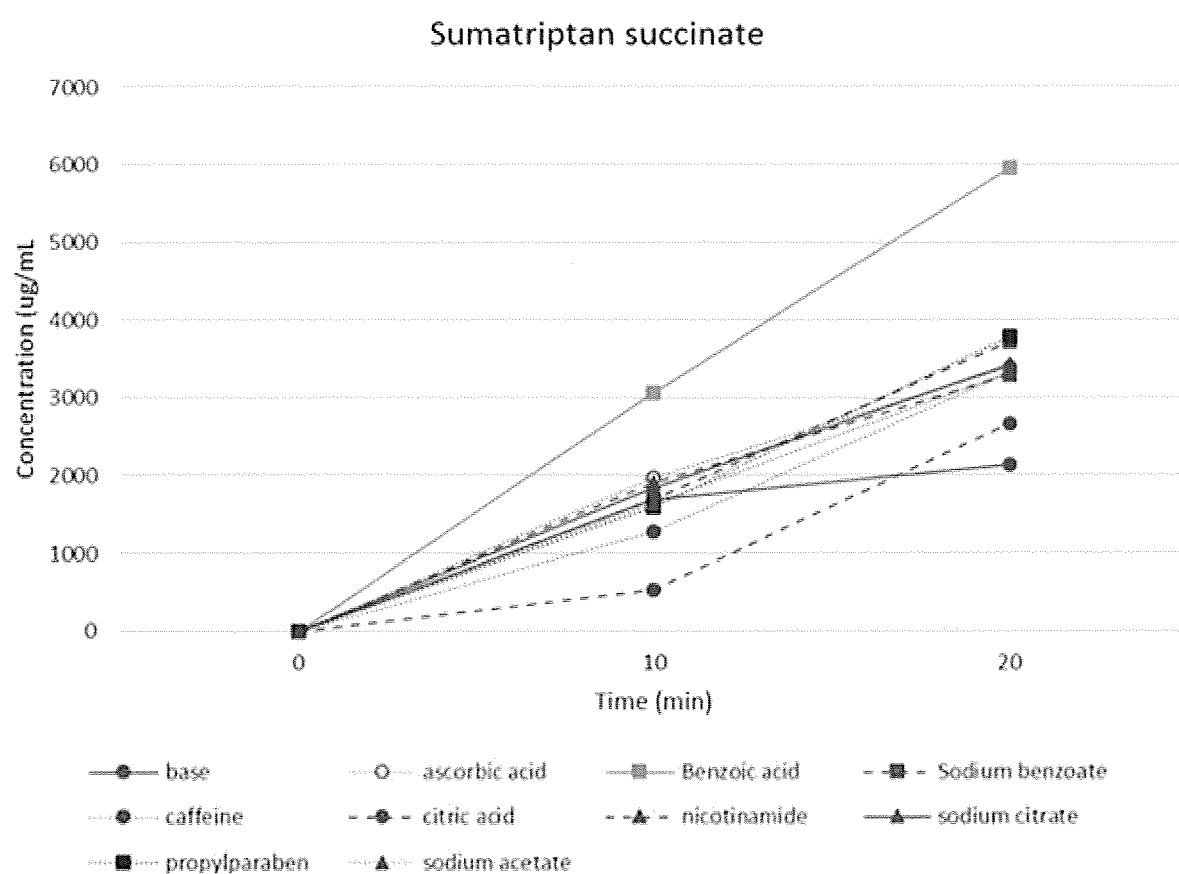
FIG. 5 is a graph of the penetration of sumatriptan succinate through an artificial membrane in the presence of various hydrotropes.
Figure 6:
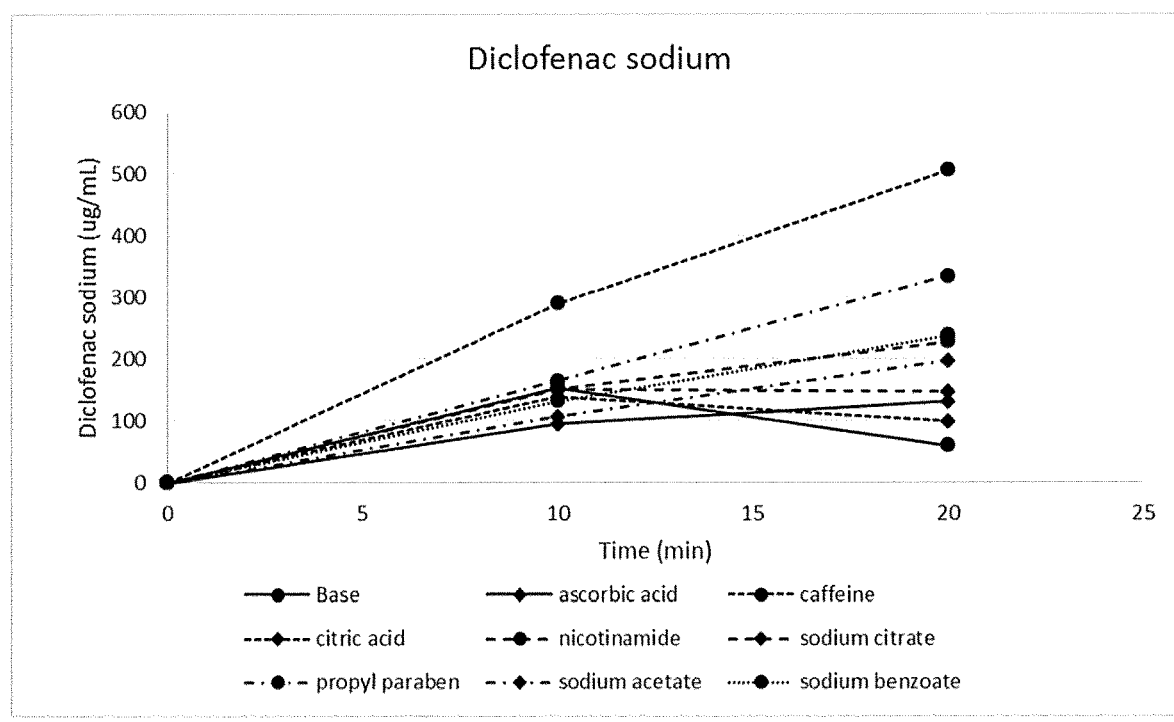
FIG. 6 is a graph of the penetration of diclofenac sodium through an artificial membrane in the presence of various hydrotropes.
Figure 7A:
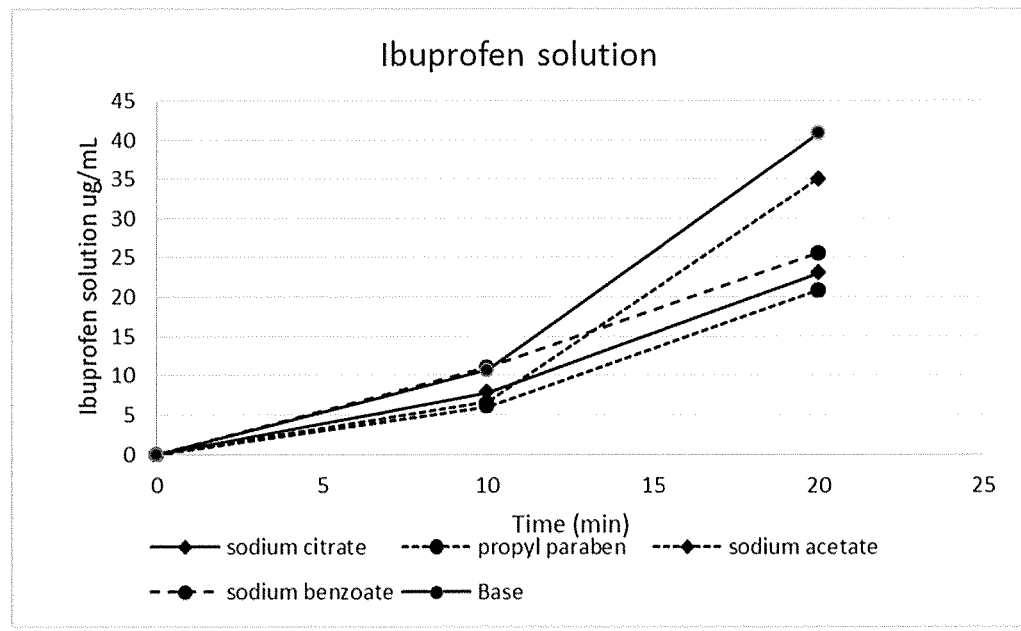
FIGS. 7A and 7B is a graph of the penetration of ibuprofen solution and suspension through an artificial membrane in the presence of various hydrotropes.
Figure 7B:
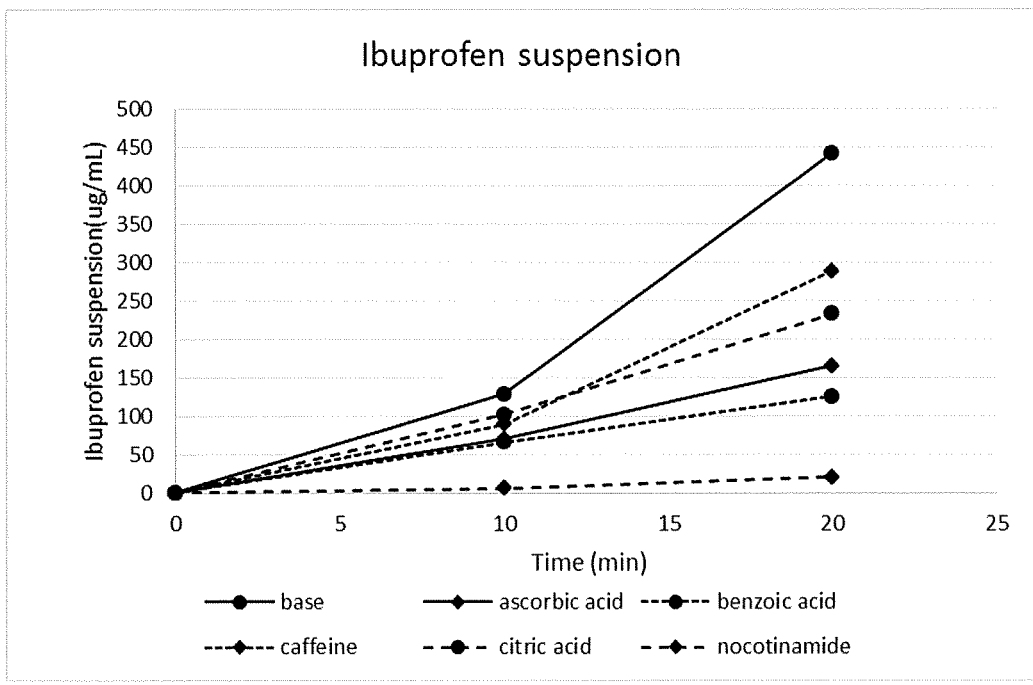
Figure 8:
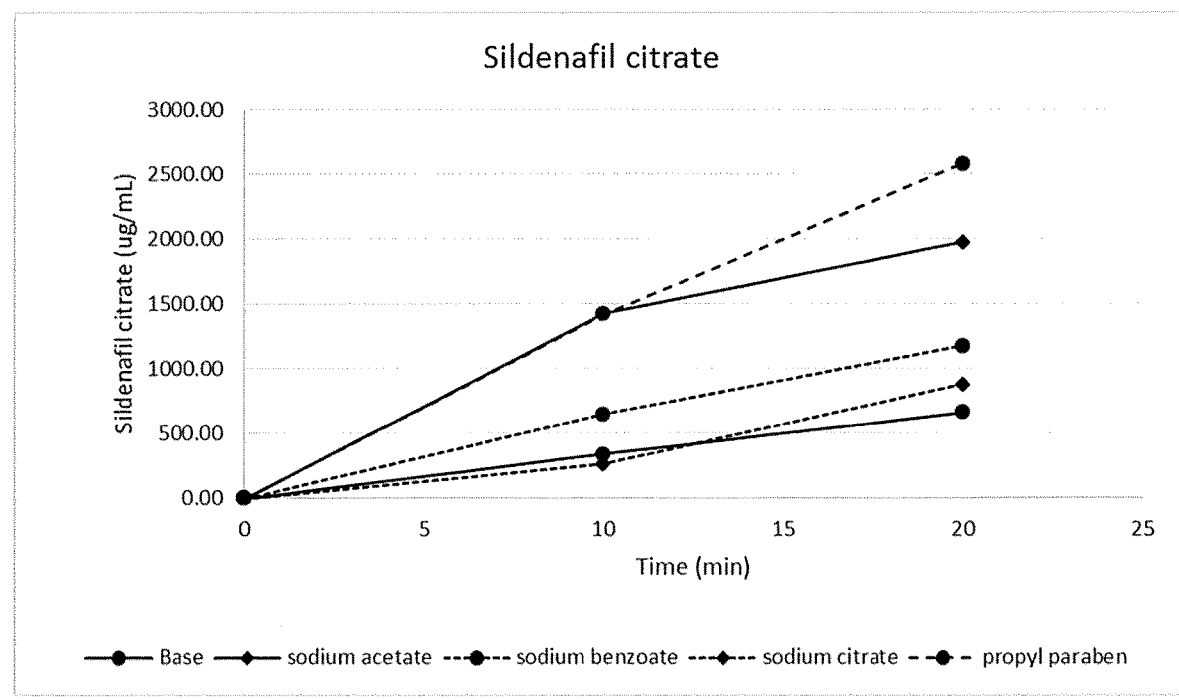
FIG. 8 is a graph of the penetration of sildenafil citrate through an artificial membrane in the presence of various hydrotropes.
Figure 9:
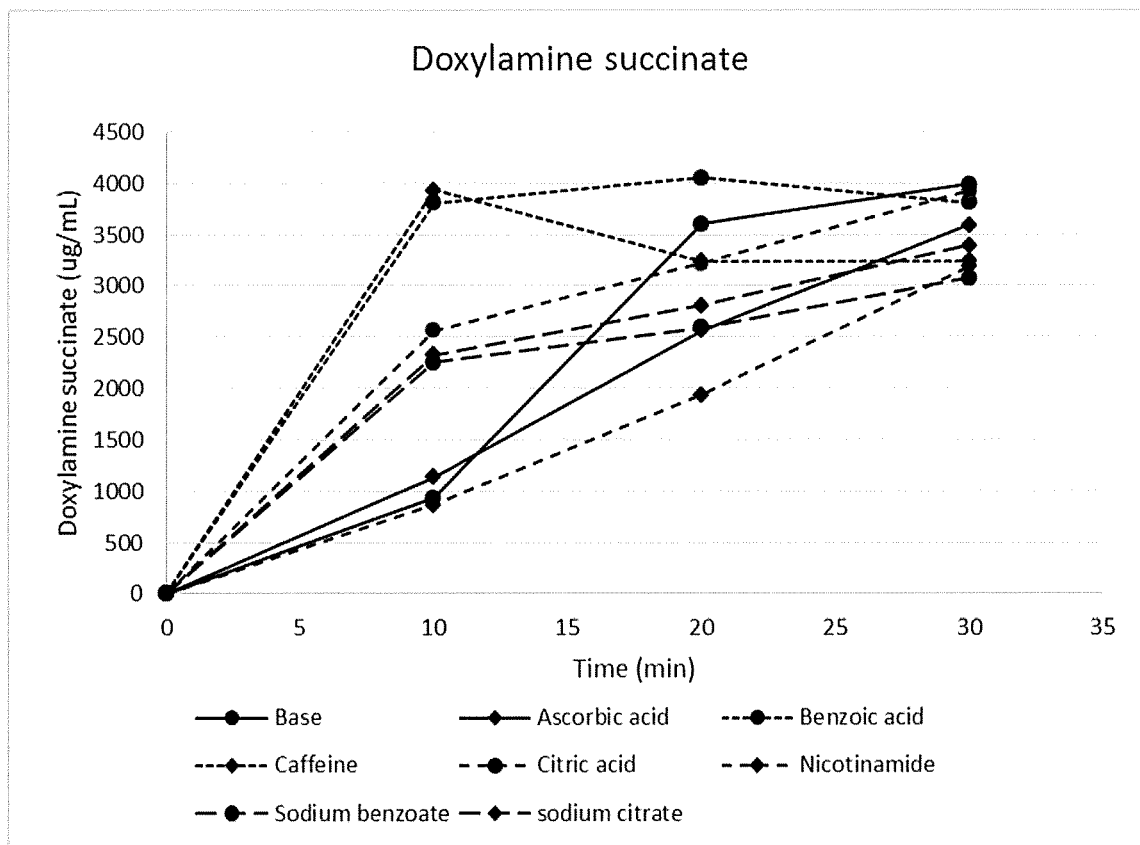
FIG. 9 is a graph of the penetration of doxylamine succinate through an artificial membrane in the presence of various hydrotropes.
Figure 10A:
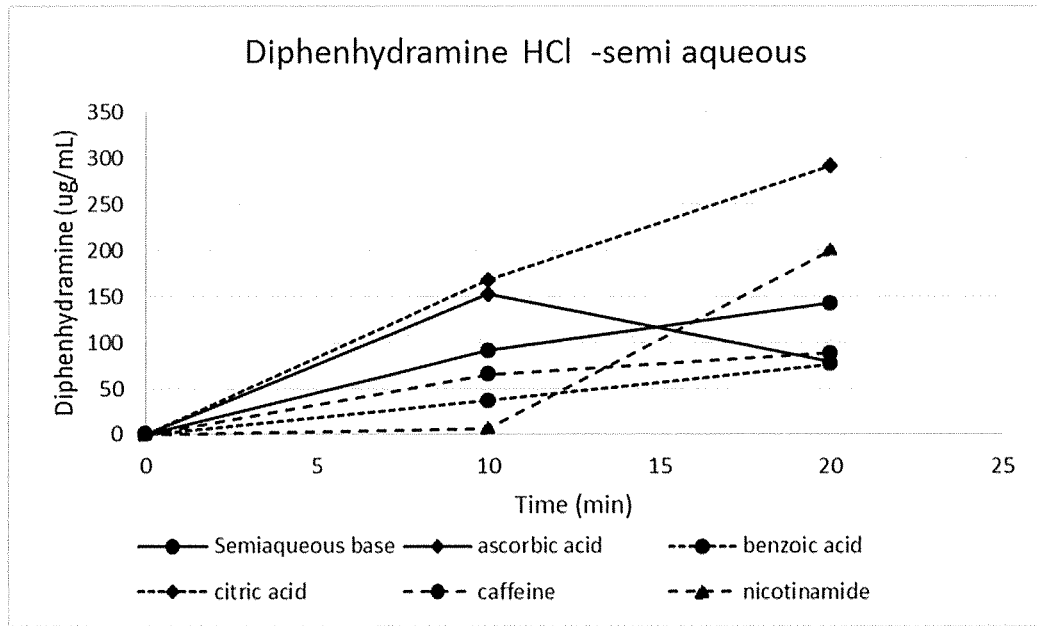
FIGS. 10A and 10B is a graph of the penetration of aqueous and semi-aqueous diphenhydramine HCl through an artificial membrane in the presence of various hydrotropes.
Figure 10B:
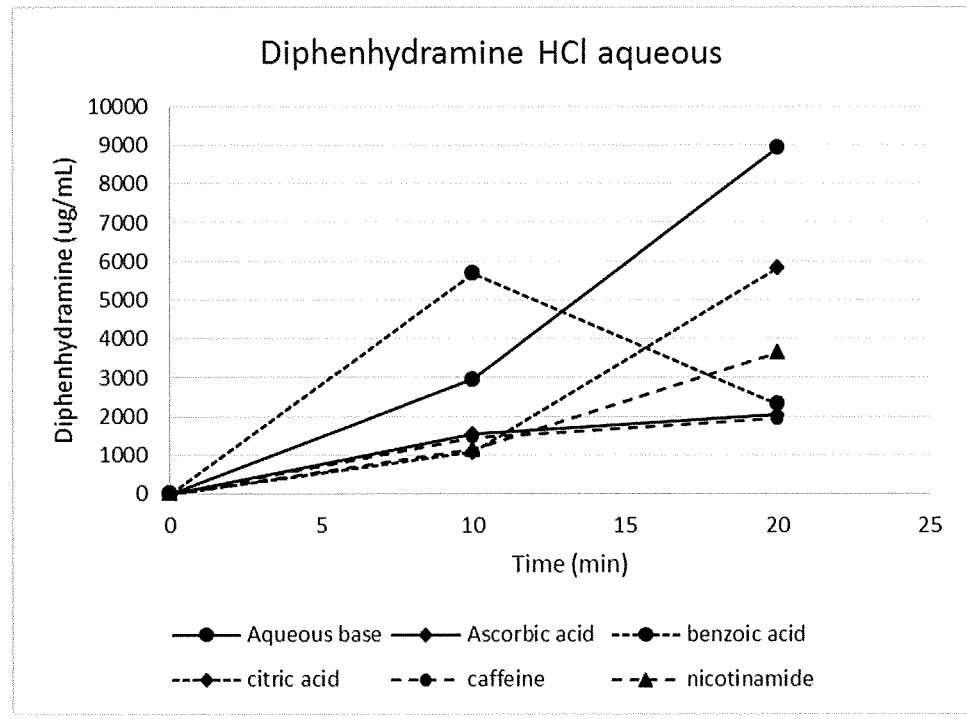

Results of the trials are provided as follows:
FIG. 3—Ondansetron (log P or log D 2.4) in various hydrotropes; nicotinamide or caffeine most effective
FIG. 4—Zolpidem (log P or log D 1.2) in in various hydrotropes; citric acid most effective
FIG. 5—Sumatriptan succinate (log P or log D 1.7) in in various hydrotropes; benzoic acid most effective
FIG. 6—Diclofenac sodium (log P or log D 4.75 hydroalcoholic solution) with various hydrotropes; caffeine most effective
FIG. 7a—Ibuprofen solution (log P or log D 3.5) with various hydrotropes; no improvement
FIG. 7a—Ibuprofen suspension (log P or log D 3.5) with various hydrotropes; no improvement
FIG. 8—Sildenafil citrate (log P or log D 1.6, pH 7) with various hydrotropes; propyl paraben most effective
FIG. 9—Doxylamine succinate (log P or log D 2.9) with various hydrotropes; benzoic acid most effective In another experiment, the effects of the formulation on the permeation enhancing abilities of the hydrotropes was performed utilising aqueous and hydroalcoholic formulations. A shift was seen in the most effective permeation enhancing hydrotrope.
FIG. 10a—Diphenhydramine HCl (log P or log D 3.5) semi aqueous with various hydrotropes; citric acid most effective
FIG. 10b—Diphenhydramine HCl (log P or log D 3.5) aqueous with various hydrotropes; benzoic acid most effective Example 2

Ex Vivo Permeability Experiments—Porcine Buccal Membranes in Franz Cells

Buccal Delivery Method

Buccal tissue from domestic pigs (Sus scrofa domestica) were obtained from a local abattoir directly after slaughter and immediately placed on ice. Within 2 hours of collection, tissue is prepared for delivery experiments.

For permeation experiments tissue is placed in pH 6.8 PBS and epithelium separated from the connective tissue using surgical dissection or by contact in solution (pH 6.8 PBS) heated to 65° C. for 60 seconds. Surgical dissection is preferred method for maintaining intact epithelia with minimal impact on integrity which can occur with heating.

After isolation, tissue is placed on Franz cell receiver chamber filled with PBS at pH optimised for permeant solubility and containing micro-stirring bar. Air bubbles are removed before donor chamber is clamped. The exposed epithelial surface is pre-incubated in pH 6.8 PBS in air incubator heated to 37° C. for minimum 15 minutes to equilibrate to temperature. All samples are continuously stirred on a magnetic plate at 300 rpm for duration of pre-incubation and subsequent permeation experiment.

After equilibration, the donor chamber buffer is removed by pipette and replaced with active agent solution to be tested. Volume of active agent solution applied is 500 ul or 1 ml.

At time 0 samples of 200 ul is removed from receiver chamber and 200 ul volume replaced with buffer. Samples taken at timed intervals (standard 15, 30, 60 minutes) are 200 ul volumes removed from side arm of receiver chamber using gel-loading pipette tips. Removed samples are placed in HPLC tubes for HPLC analysis. After each sample is taken the 200 ul volume is replaced with PBS pH 4.5 buffer to maintain constant volume in receiver chamber (which will dilute slightly each subsequent sample).

TABLE 4

Percentage composition of experimental sildenafil formulations containing hydrotropes

| Formulation | Base | F1 | F2 | F3 | F4 |
|---|---|---|---|---|---|
| Sildenafil citrate | 11.67 | 11.67 | 11.67 | 11.67 | 11.67 |
| Propylene glycol | 52.14 | 10 | 10 | 10 | 10 |
| Ethanol | 24.09 | 30 | 30 | 30 | 30 |
| 10% by weight Hydrochloric acid | 10 | 15 | 15 | 15 | 15 |
| 5M Sodium Hydroxide | 2.1 | — | — | 2.1 | — |
| Caffeine | — | 1.25 | 2.5 | 2.5 | 2.5 |
| Nicotinamide | — | 5.0 | — | 0.05 | 7.5 |
| Ascorbic acid | — | — | 4.0 | — | — |
| Water | — | 27 | 20 | 28.68 | 22 |
| TOTAL | 100 | 100 | 100 | 100 | 100 |

Figure 11A:
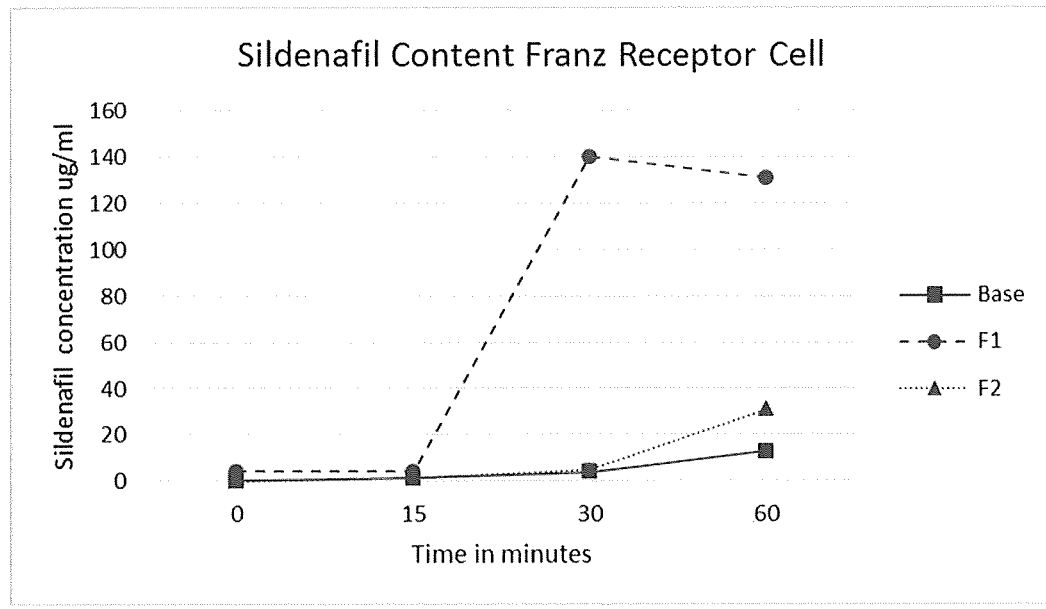
FIGS. 11A and 11B are graphs of the penetration of sildenafil citrate in combination with various hydrotrope mixtures according to the present invention after permeation through porcine buccal mucosa.
Figure 11B:
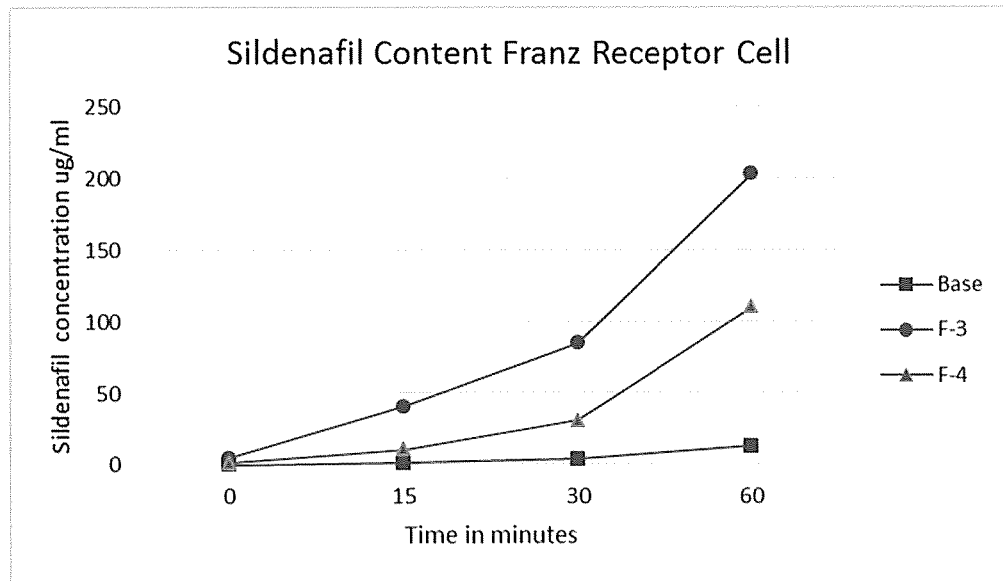

The results are provided in FIGS. 11A and 11B. The results show Class A hydrotrope caffeine has limited effect on the early permeation but increases total permeation.

Figure 12:
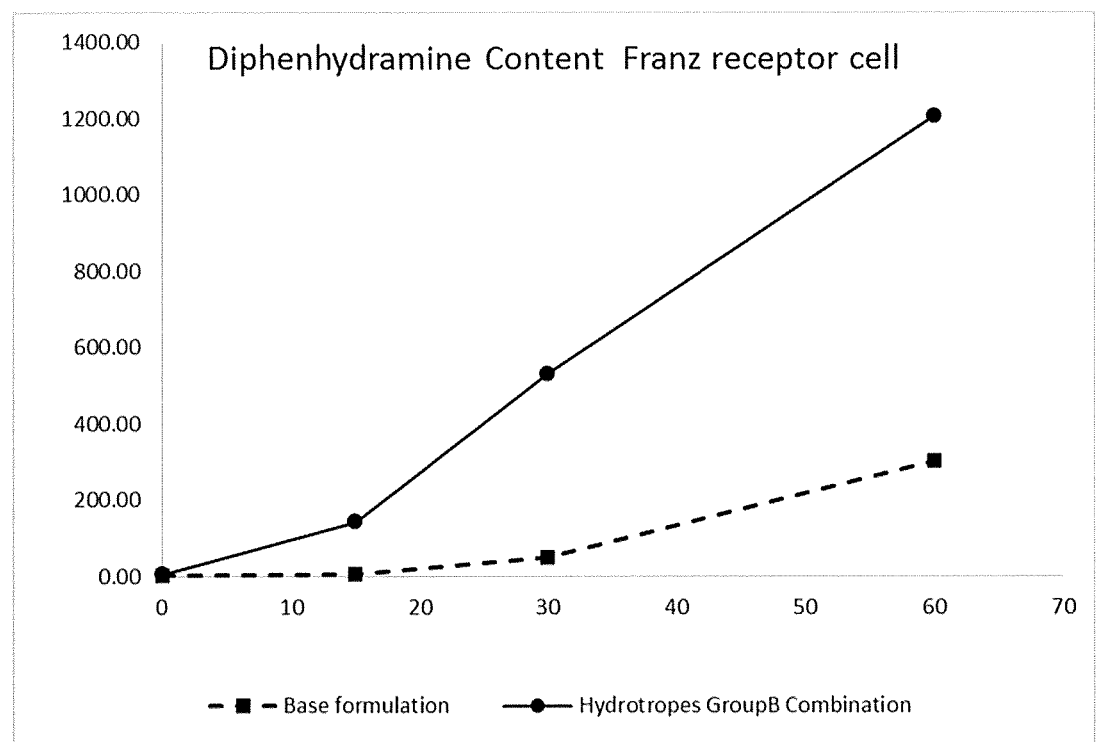
FIG. 12 is a graph of the penetration of diphenhydramine HCl through an artificial membrane in the presence of a hydrotrope combination.

In another experiment, diphenhydramine (after being run through the preliminary single hydrotrope screen) was formulated with two Class B hydrotropes, sweeteners and flavours and screened in the ex vitro porcine buccal membrane against the same formulation minus the hydrotrope content. The results are provided in FIG. 12 and show a large increase both in early permeation and in total permeation.

Figure 13:
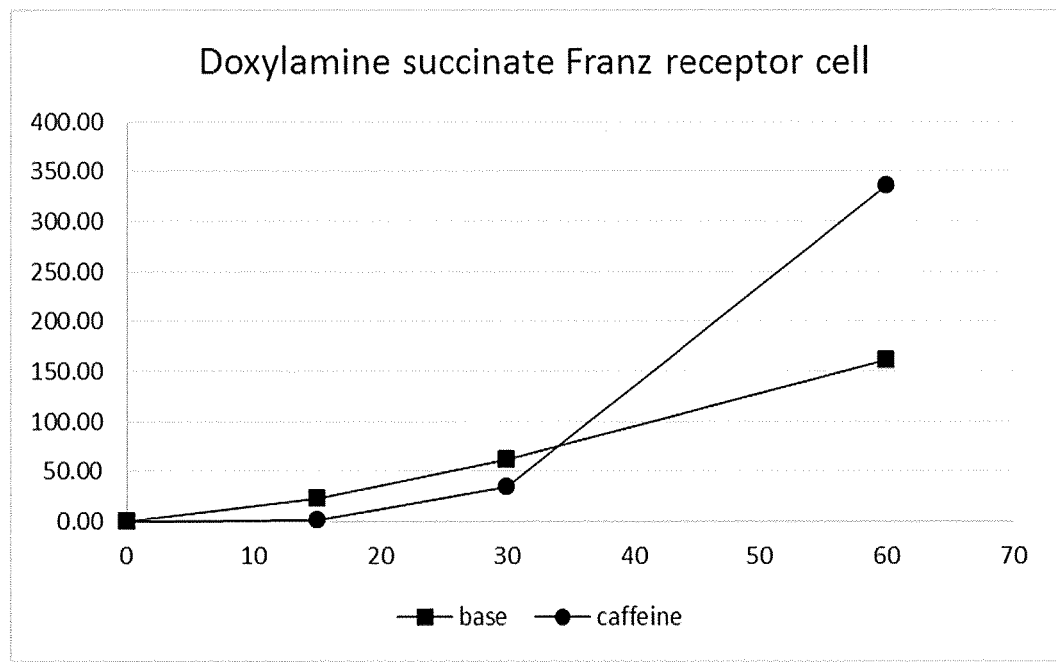
FIG. 13 is a graph of the penetration of doxylamine succinate through an artificial membrane in the presence of the hydrotrope caffeine.

In another experiment, doxylamine (after being run through the preliminary single hydrotrope screen) was formulated with the Class A hydrotrope caffeine, plus sweeteners and flavours and screened in the ex vitro porcine buccal membrane against the same formulation minus the hydrotrope content. The results are provided in FIG. 13 show caffeine does not affect the early permeation but increases total permeation.

Example 3

In Vivo Studies in Rabbits

Ten male rabbits (*Oryctolagus cuniculus*) Strain New Zealand White (NZW) aged 8-12 weeks were delivered 5 days prior to the experiment for acclimatisation. The animals were kept in a controlled environment (targeted ranges: temperature 21±3° C., humidity 30-70%), with a light/dark cycle each of 12 hours, and under barrier (quarantine) conditions. Temperature and relative humidity was monitored continuously throughout the study duration. Feed consisted of Rabbit and Guinea Pig pellets. Municipal town water was supplied ad libitum. Dietary enrichment was provided during the acclimation period in the form of fresh fruit and vegetables. Enrichment items were not provided following randomisation into study groups and during dose administration.

Procedures involving the care and use of animals in this study were reviewed and approved by the La Trobe University Animal Ethics Committee prior to conduct. During the study, the care and use of animals will be conducted in accordance with the principles outlined in the Australian Code of Practice for the Care and Use of Animals for Scientific Purposes, 8th Edition, 2013 (National Health and Medical Research Council). The study was carried out according to the approval conditions of the LTU AEC.

Prior to dose administration, a total of ten male NZW rabbits were randomized into two groups of five based on body weight. Each animal group was allocated to receive a different sildenafil Formulation (either sildenafil Formulation 4 (F4) or sildenafil Base formulation (see Example 2)). On study day 1, animals underwent central ear artery catheterisation that was maintained for 4 h to avoid repeated punctures blood sampling. On study day 1, rabbits were buccally administered as a single dose of 20 mg (2×0.12 mL aliquots) of either F4 or Base. Buccal administration consisted of a measured dose of the Formulation (0.12 mL, 10 mg Sildenafil) applied onto the non-keratinised section of cheek interior of the unconscious/deeply sedated rabbit using a plastic pipette. Contact time of 1 min was allowed and the rabbit was turned onto its other side and the procedure repeated for the other cheek.

PK arterial blood samples were collected via central ear artery pre-dose, 10, 15, 20, 30, 45, 60, 120 and 240 min following Formulation administration. Animals were euthanized and discarded after the final bleed.

TABLE 5

Study design

| Group | Animal Number and Gender | Test Article | Dose | Route | Bleeding Time Points (min) | Termination Study Day |
|---|---|---|---|---|---|---|
| 1 | 5x Male | Sildenafil F4 | 2 × 0.12 mL 20 mg/day | p.o | 0, 10, 15, 20, 30, 45, 60, 120 and 240 | 1 |
| 2 | 5x Male | Sildenafil base | 2 × 0.12 mL 20 mg/day | p.o | 0, 10, 15, 20, 30, 45, 60, 120 and 240 | 1 |

Portions of whole blood (400 μL) were collected into $K_2$EDTA blood tubes then centrifuged and the resulting at −80° C. prior to analysis by LC-MS/MS. Peak concentration in blood ($C_{max}$), Time to reach $C_{max}$ ($T_{max}$), half-life ($t_{1/2}$) and area under curve (AUC) were calculated.

Figure 14:
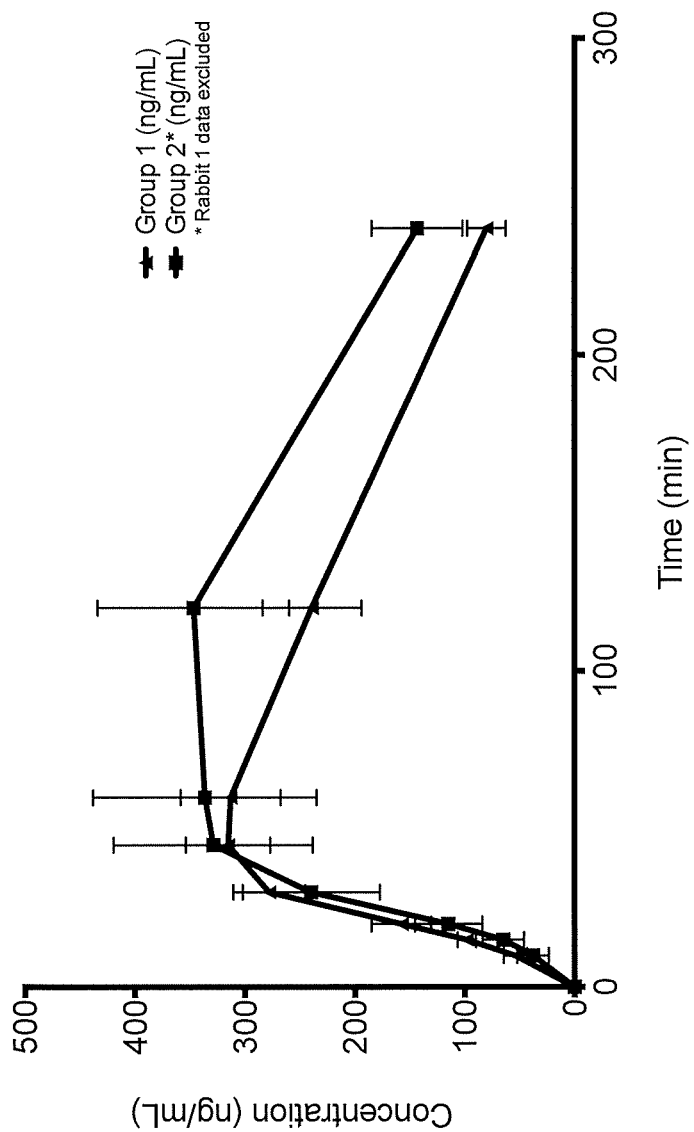
FIG. 14 is a graph of the penetration of sildenafil through rabbit buccal mucosa in the presence of a combination of two hydrotropes; 2.5% caffeine and 7.5% nicotinamide. Base formulation—Group 1: triangle; F4—Group 2: square.

The results are shown in FIG. 14. The Figures shows that the presence of 2.5% caffeine and 7.5% nicotinamide (Group 2) resulted in a marked increase in the bioavailability of sildenafil in comparison to the Base formulation (Group 1).

Figure 15:
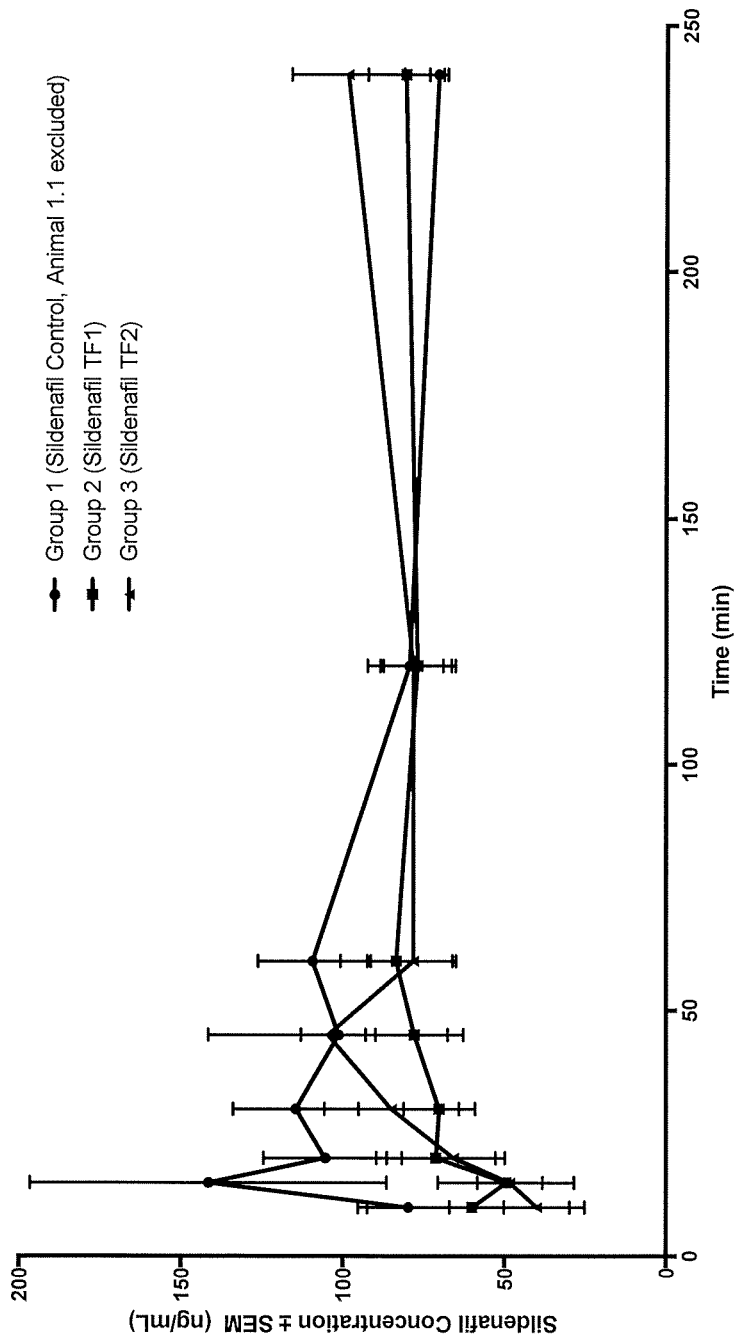
FIG. 15 is a graph of the penetration of sildenafil through rabbit buccal mucosa in the presence of a combination of two hydrotropes; 1.25% caffeine and 3.75% nicotinamide.

The ability of the Class A hydrotropes to maintain a sustained release is illustrated by a second experiment (FIG. 15) with a different caffeine/nicotinamide (1.25%/3.75%) combination which results in a pronounced sustained release. The sildenafil-hydrotrope combination was still increasing in plasma concentration at 250 min, in contrast to the control in which plasma concentration of sildenafil had begun to decrease. The two formulations, TF1 and TF2, differ only in flavour combinations.

The invention claimed is:

1. A method to increase the penetration of an active agents through an oral mucosal membrane, the method comprising the step of:
   a) administering to a subject in need an oral spray composition comprising:
   a Class A and a Class B hydrotrope in a total amount of less than 10% by weight of the composition; and
   ii) a BCS Class III active agent with a partition co-efficient (log P) or distribution co-efficient (log D) of between 0 and 3.5,
   wherein
   the BCS class III active agent is sumatriptan or any pharmaceutically acceptable salt thereof;
   the class A hydrotrope is caffeine; and
   the class B hydrotrope is sodium acetate.

2. A kit for increasing the penetration of an active agent through an oral mucosal membrane containing:
   a) an oral spray composition comprising
   i) a Class A and a Class B hydrotrope in a total amount of less than 10% by weight of the composition; and
   ii) a BCS Class III active agent with a partition co-efficient (log P) or distribution co-efficient (log D) of between 0 and 3.5,
   wherein
   the BCS class III active agent is sumatriptan or any pharmaceutically acceptable salt thereof;
   the class A hydrotrope is caffeine; and
   the class B hydrotrope is sodium acetate.

3. The method of claim 1 wherein the composition further comprises a co-solvent.

4. The method of claim 1 wherein the composition further comprises one or more pharmaceutically acceptable excipients.

5. The method of claim 1 wherein the log P or log D is between 0.9 and 3.5; or between 2.5 and 3.5; or between 0.5 and 3.0.

6. The method of claim 1 wherein the hydrotrope does not increase the solubility of the active agent.

7. The method of claim 1 wherein the hydrotrope is present in the composition at a total amount of less than 9%, 8%, 7%, 6%, 5%, 4%, 3%, 2%, 1%, 0.5% or 0.25% by weight of the composition.

8. An oral spray composition for increasing the penetration of an active agent through an oral mucosal membrane comprising:
 a) a Class A and a Class B hydrotrope in a total amount of less than 10% by weight of the composition; and
 b) a BCS Class III active agent with a partition co-efficient (log P) or distribution co-efficient (log D) of between 0 and 3.5,
 wherein
  the BCS class III active agent is sumatriptan or any pharmaceutically acceptable salt thereof;
  the class A hydrotrope is caffeine; and
  the class B hydrotrope is sodium acetate.

\* \* \* \* \*